(12) United States Patent
Leon et al.

(10) Patent No.: US 11,434,291 B2
(45) Date of Patent: Sep. 6, 2022

(54) METHODS AND COMPOSITIONS FOR PREVENTING TYPE 1 DIABETES

(71) Applicant: Provention Bio, Inc., Lebanon, NJ (US)

(72) Inventors: Francisco Leon, Bethesda, MD (US); Kevan C. Herold, Norwalk, CT (US); Jay S. Skyler, Key Biscayne, FL (US)

(73) Assignee: Provention Bio, Inc., Red Bank, NJ (US)

( * ) Notice: Subject to any disclaimer, the term of this patent is extended or adjusted under 35 U.S.C. 154(b) by 0 days.

(21) Appl. No.: 15/931,685

(22) Filed: May 14, 2020

(65) Prior Publication Data

US 2020/0399368 A1 Dec. 24, 2020

Related U.S. Application Data

(60) Provisional application No. 62/847,466, filed on May 14, 2019.

(51) Int. Cl.
*C07K 16/28* (2006.01)
*A61P 3/10* (2006.01)
*A61K 9/00* (2006.01)

(52) U.S. Cl.
CPC ........ *C07K 16/2809* (2013.01); *A61K 9/0019* (2013.01); *A61K 9/0053* (2013.01); *A61P 3/10* (2018.01)

(58) Field of Classification Search
CPC .............................. C07K 16/2809; A61P 3/10
See application file for complete search history.

(56) References Cited

U.S. PATENT DOCUMENTS

| | | | |
|---|---|---|---|
| 5,885,573 A | 3/1999 | Bluestone et al. | |
| 6,491,916 B1 | 12/2002 | Bluestone et al. | |
| 6,723,538 B2 | 4/2004 | Mack et al. | |
| 6,905,685 B2 | 6/2005 | Kwon | |
| 6,956,041 B2 | 10/2005 | Blumenkopf et al. | |
| 7,041,289 B1 | 5/2006 | Bach et al. | |
| 7,091,208 B2 | 8/2006 | Blumenkopf et al. | |
| 7,235,641 B2 | 6/2007 | Kufer et al. | |
| 7,262,276 B2 | 8/2007 | Huang et al. | |
| 7,304,033 B2 | 12/2007 | Larsen et al. | |
| 7,395,158 B2 | 7/2008 | Monfre et al. | |
| 7,482,327 B2 | 1/2009 | Hagerty et al. | |
| 7,563,869 B2 | 7/2009 | Honjo et al. | |
| 7,569,569 B2 | 8/2009 | Blumenkopf et al. | |
| 7,592,313 B2 | 9/2009 | Zheng et al. | |
| 7,612,181 B2 | 11/2009 | Chengbin et al. | |
| 7,635,472 B2 | 12/2009 | Kuler et al. | |
| 7,714,103 B2 | 5/2010 | Levetan et al. | |
| 7,728,114 B2 | 6/2010 | Mach et al. | |
| 7,744,863 B1 | 6/2010 | Hall et al. | |
| 7,820,166 B2 | 10/2010 | Lanzavecchia | |
| 7,883,703 B2 | 2/2011 | Weiner et al. | |
| 7,919,089 B2 | 4/2011 | Kufer et al. | |
| 7,989,415 B2 | 8/2011 | Levetan et al. | |
| 7,998,479 B2 | 8/2011 | Honjo et al. | |
| 8,007,796 B2 | 8/2011 | Baeuerle et al. | |
| 8,076,459 B2 | 12/2011 | Hofmeister et al. | |
| 8,101,722 B2 | 1/2012 | Kufer et al. | |
| 8,182,812 B2 | 5/2012 | Schuurman et al. | |
| 8,211,430 B2 | 7/2012 | Levetan et al. | |
| 8,211,440 B2 | 7/2012 | Chang et al. | |
| 8,246,955 B2 | 8/2012 | Honjo et al. | |
| 8,246,960 B2 | 8/2012 | Chang et al. | |
| 8,258,268 B2 | 9/2012 | Wu et al. | |
| 8,383,578 B2 | 2/2013 | Levetan et al. | |
| 8,394,926 B2 | 3/2013 | Lutterbuse et al. | |
| 8,398,995 B2 | 3/2013 | Rottiers et al. | |
| 8,420,081 B2 | 4/2013 | Fraunhofer et al. | |
| 8,481,022 B2 | 7/2013 | Lodie et al. | |
| 8,530,629 B2 | 9/2013 | Chang | |
| 8,551,478 B2 | 10/2013 | Mach et al. | |
| 8,586,714 B2 | 11/2013 | Ghayur et al. | |
| 8,623,830 B2 | 1/2014 | Flier et al. | |
| 8,663,634 B2 | 3/2014 | Koenig et al. | |
| 8,735,553 B1 | 5/2014 | Li et al. | |
| 8,785,400 B2 | 7/2014 | Levetan et al. | |
| 8,790,645 B2 | 7/2014 | Kufer et al. | |

(Continued)

FOREIGN PATENT DOCUMENTS

| | | | |
|---|---|---|---|
| EP | 1515749 B1 | 3/2005 | |
| EP | 1591527 B1 | 11/2005 | |

(Continued)

OTHER PUBLICATIONS

Long et al. Partial exhaustion of CD8 T cells and clinical response to teplizumab in new-onset type 1 diabetes.Sci Immunol. Nov. 2016; 1(5). (Year: 2016).*
American Diabetes Association, "2. Classification and Diagnosis of Diabetes: Standards of Medical Care in Diabetes—2019" Diabetes Care, vol. 42, Suppl. 1, pp. S13-S28, Jan. 2019.
Atkinson et al., "The Challenge of Modulating Beta-Cell Autoimmunity in Type 1 Diabetes" Lancet Diabetes Endocrinol, vol. 7, pp. 52-64, 2019.
Bingley et al., "Type 1 Diabetes TrialNet: A Multifaceted Approach to Bringing Disease-Modifying Therapy to Clinical Use in Type 1 Diabetes" Diabetes Care, vol. 41, pp. 653-661, Apr. 2018.
Cox D., "Regression Models and Life Tables" Journal of the Royal Statistical Society, Series B, vol. 34, No. 2, pp. 187-220, 1972.
Demeester et al., "Preexisting Insulin Autoantibodies Predice Efficacy of Otelixizumab in Preserving Residual beta-Cell Function in Recent-Onset Type 1 Diabetes" Diabetese Care, vol. 3, No. 4, pp. 644-651, Apr. 2015.

(Continued)

*Primary Examiner* — Daniel E Kolker
*Assistant Examiner* — Brian Hartnett
(74) *Attorney, Agent, or Firm* — Greenberg Traurig, LLP; David J. Dykeman; Fang Xie

(57) ABSTRACT

Provided herein, in one aspect, is a method of preventing or delaying the onset of clinical type 1 diabetes (T1D), comprising: providing a non-diabetic subject who is at risk for T1D; determining that the non-diabetic subject (1) is substantially free of antibodies against zinc transporter 8 (ZnT8), (2) is HLA-DR4+, and/or (3) is not HLA-DR3+; and administering a prophylactically effective amount of an anti-CD3 antibody to the non-diabetic subject.

20 Claims, 12 Drawing Sheets

Specification includes a Sequence Listing.

(56) References Cited

U.S. PATENT DOCUMENTS

| | | |
|---|---|---|
| 8,808,689 B1 | 8/2014 | Levetan |
| 8,816,047 B2 | 8/2014 | Levetan et al. |
| 8,846,873 B2 | 9/2014 | Xiao et al. |
| 8,883,146 B2 | 11/2014 | Fraunhofer et al. |
| 8,932,586 B2 | 1/2015 | Jones et al. |
| 8,951,518 B2 | 2/2015 | Honjo et al. |
| 8,980,244 B2 | 3/2015 | Mandelboim et al. |
| 8,987,425 B2 | 3/2015 | Lee et al. |
| 9,056,906 B2 * | 6/2015 | Koenig ............... A61P 1/00 |
| 9,079,965 B2 | 7/2015 | Lewyn et al. |
| 9,085,619 B2 | 7/2015 | Fraunhofer et al. |
| 9,089,531 B2 | 7/2015 | Kaufman et al. |
| 9,102,736 B2 | 8/2015 | Hofmeister et al. |
| 9,192,665 B2 | 11/2015 | Zugmaier et al. |
| 9,217,034 B2 | 12/2015 | Li et al. |
| 9,226,962 B2 | 1/2016 | LeGall et al. |
| 9,249,211 B2 | 2/2016 | Schellenberger et al. |
| 9,296,815 B2 | 3/2016 | D'Angelo et al. |
| 9,308,257 B2 | 4/2016 | Sharma et al. |
| 9,315,585 B2 | 4/2016 | Cheung et al. |
| 9,321,812 B2 | 4/2016 | Levetan |
| 9,371,517 B2 | 6/2016 | Jones et al. |
| 9,382,329 B2 | 7/2016 | Chang et al. |
| 9,447,387 B2 | 9/2016 | Jones et al. |
| 9,447,431 B2 | 9/2016 | Thess et al. |
| 9,453,052 B2 | 9/2016 | Gmber et al. |
| 9,474,744 B2 | 10/2016 | Cohen et al. |
| 9,493,563 B2 | 11/2016 | Blein et al. |
| 9,511,110 B2 | 12/2016 | Levetan |
| 9,562,110 B2 | 2/2017 | Zhou et al. |
| 9,574,010 B2 | 2/2017 | Spreter Von Kreudenstein et al. |
| 9,587,021 B2 | 3/2017 | Huang et al. |
| 9,611,325 B2 | 4/2017 | Zhou et al. |
| 9,616,105 B2 | 4/2017 | Paulsen et al. |
| 9,670,286 B2 | 6/2017 | Chang et al. |
| 9,682,143 B2 | 6/2017 | Chang et al. |
| 9,688,772 B2 | 6/2017 | Cheung et al. |
| 9,695,250 B2 | 7/2017 | Lutterbuse et al. |
| 9,701,749 B2 | 7/2017 | Shibayama et al. |
| 9,708,412 B2 | 7/2017 | Baeuerle et al. |
| 9,777,073 B2 | 7/2017 | Shibayama et al. |
| 9,783,609 B2 | 10/2017 | Honjo et al. |
| 9,802,995 B2 | 10/2017 | Ahmed et al. |
| 9,820,955 B2 | 11/2017 | Kaufman et al. |
| 9,850,304 B2 | 12/2017 | Mach et al. |
| 9,879,088 B2 | 1/2018 | Chang et al. |
| 9,982,063 B2 | 5/2018 | Lutterbuse et al. |
| 9,987,356 B2 | 6/2018 | Reimann et al. |
| 10,000,567 B2 | 6/2018 | Ellis et al. |
| 10,000,574 B2 | 6/2018 | Hofmeister et al. |
| 10,010,577 B2 | 7/2018 | Levetan |
| 10,010,578 B2 | 7/2018 | Levetan |
| 10,010,579 B2 | 7/2018 | Levetan |
| 10,010,580 B2 | 7/2018 | Levetan |
| 10,016,482 B2 | 7/2018 | Levetan |
| 10,022,440 B2 | 7/2018 | Wasserfall et al. |
| 10,023,639 B2 | 7/2018 | Li et al. |
| 10,059,767 B2 | 8/2018 | Protzer et al. |
| 10,081,809 B2 | 9/2018 | Monteleone et al. |
| 10,086,046 B2 | 10/2018 | Paulsen et al. |
| 10,093,736 B2 | 10/2018 | Sahin et al. |
| 10,106,623 B2 | 10/2018 | Uhlin et al. |
| 10,111,968 B2 | 10/2018 | Thess et al. |
| 10,118,964 B2 | 11/2018 | Zhou et al. |
| 10,130,638 B2 | 11/2018 | Zugmaier et al. |
| 10,150,812 B2 | 12/2018 | Huang et al. |
| 10,159,710 B2 | 12/2018 | Gruber et al. |
| 10,167,341 B2 | 1/2019 | Cheung et al. |
| 10,191,034 B2 | 1/2019 | Nagorsen |
| 10,239,952 B2 | 3/2019 | Scheinberg et al. |
| 10,251,934 B2 | 4/2019 | Elliman |
| 10,266,608 B2 | 4/2019 | Wu |
| 10,272,050 B2 | 4/2019 | Farokhzad et al. |
| 10,280,425 B2 | 5/2019 | Chen et al. |
| 10,287,365 B2 | 5/2019 | Cheung et al. |
| 10,301,389 B2 | 5/2019 | Ho et al. |
| 10,316,093 B2 | 6/2019 | Cheung et al. |
| 10,329,314 B2 | 6/2019 | Fan et al. |
| 10,329,350 B2 | 6/2019 | Daute et al. |
| 10,369,114 B2 | 8/2019 | Schentag et al. |
| 10,376,518 B2 | 8/2019 | Ellis et al. |
| 10,378,055 B2 | 8/2019 | Ferreri et al. |
| 10,413,605 B2 | 9/2019 | Christen et al. |
| 10,434,078 B2 | 10/2019 | Kaufman et al. |
| 10,443,056 B2 | 10/2019 | Monteleone et al. |
| 10,449,170 B2 | 10/2019 | Venn-Watson |
| 10,465,003 B2 | 11/2019 | Hedrick et al. |
| 10,487,098 B2 | 11/2019 | Fan et al. |
| 10,519,248 B2 | 12/2019 | Cheung et al. |
| 10,548,929 B2 | 2/2020 | Champion et al. |
| 10,556,964 B2 | 2/2020 | Zhou et al. |
| 10,570,103 B2 | 2/2020 | Beaton et al. |
| 10,584,180 B2 | 3/2020 | Gruber |
| 10,590,182 B2 | 3/2020 | Lim et al. |
| 10,633,440 B2 | 4/2020 | Bonvini et al. |
| 10,640,576 B2 | 5/2020 | Jang et al. |
| 10,647,768 B2 | 5/2020 | Johnson et al. |
| 10,647,770 B2 | 5/2020 | Shibayama et al. |
| 10,662,243 B2 | 5/2020 | Nagorsen et al. |
| 10,662,252 B2 | 5/2020 | Chang et al. |
| 10,688,186 B2 | 6/2020 | Shalibhai |
| 10,696,744 B2 | 6/2020 | Zugmaier et al. |
| 10,717,780 B2 | 7/2020 | Sahin et al. |
| 10,730,880 B2 | 8/2020 | Allen et al. |
| 10,730,943 B2 | 8/2020 | Protzer et al. |
| 10,745,478 B2 | 8/2020 | Sirianni et al. |
| 10,752,686 B2 | 8/2020 | Ma et al. |
| 10,772,917 B2 | 9/2020 | Kieffer et al. |
| 10,772,958 B2 | 9/2020 | Yu et al. |
| 10,806,787 B2 | 10/2020 | Kudo et al. |
| 10,849,945 B2 | 12/2020 | Champion et al. |
| 10,858,663 B2 | 12/2020 | Rottiers et al. |
| 10,865,230 B2 | 12/2020 | Liu et al. |
| 10,882,909 B2 | 1/2021 | Ho et al. |
| 10,905,727 B2 | 2/2021 | Rottiers et al. |
| 10,925,972 B2 | 2/2021 | Demetriou et al. |
| 10,940,151 B2 | 3/2021 | Friedman et al. |
| 10,961,315 B2 | 3/2021 | Liu |
| 10,973,889 B2 | 4/2021 | Kjellman et al. |
| 10,975,112 B2 | 4/2021 | Zhao |
| 10,980,890 B2 | 4/2021 | Kim et al. |
| 11,008,601 B2 | 5/2021 | Wang et al. |
| 11,026,994 B2 | 6/2021 | Elliman |
| 11,029,317 B2 | 6/2021 | Sarwal et al. |
| 11,046,745 B2 | 6/2021 | Sahin et al. |
| 11,046,768 B2 | 6/2021 | Cheung et al. |
| 11,052,052 B2 | 7/2021 | Schentag et al. |
| 11,065,343 B2 | 7/2021 | Park et al. |
| 11,066,476 B2 | 7/2021 | Fang et al. |
| 11,084,876 B2 | 8/2021 | Kufer et al. |
| 11,091,547 B2 | 8/2021 | Ferrone et al. |
| 11,098,079 B2 | 8/2021 | Hoang et al. |
| 11,098,115 B2 | 8/2021 | Willemsen et al. |
| 11,123,438 B2 | 9/2021 | Li et al. |
| 11,124,568 B1 | 9/2021 | Ahmed et al. |
| 11,124,578 B2 | 9/2021 | Heusser et al. |
| 11,147,886 B2 | 10/2021 | Ng et al. |
| 11,154,617 B2 | 10/2021 | Baeuerle et al. |
| 11,155,622 B2 | 10/2021 | Brown et al. |
| 11,160,876 B2 | 11/2021 | Markovic et al. |
| 11,161,906 B2 | 11/2021 | Lowman et al. |
| 11,167,040 B2 | 11/2021 | Kim et al. |
| 11,173,214 B2 | 11/2021 | Kim et al. |
| 11,174,323 B2 | 11/2021 | Marasco et al. |
| 11,186,638 B2 | 11/2021 | Snell et al. |
| 11,193,155 B2 | 12/2021 | Wang et al. |
| 11,220,551 B2 | 1/2022 | Moffat et al. |
| 11,306,142 B2 | 4/2022 | Nathwani et al. |
| 11,311,631 B2 | 4/2022 | Markovic et al. |
| 2001/0044416 A1 | 11/2001 | McCluskie et al. |
| 2002/0006403 A1 | 1/2002 | Yu et al. |
| 2003/0017979 A1 | 1/2003 | Mack et al. |
| 2003/0083472 A1 | 5/2003 | Tamatani et al. |
| 2003/0108548 A1 | 6/2003 | Bluestone et al. |

(56) References Cited

U.S. PATENT DOCUMENTS

| | | |
|---|---|---|
| 2003/0194403 A1 | 10/2003 | van de Winkel et al. |
| 2003/0216551 A1 | 11/2003 | Delovitch |
| 2003/0235583 A1 | 12/2003 | Sturis et al. |
| 2004/0023885 A1 | 2/2004 | Brand et al. |
| 2004/0024208 A1 | 2/2004 | Das et al. |
| 2004/0037826 A1 | 2/2004 | Michelsen et al. |
| 2004/0054186 A1 | 3/2004 | Das et al. |
| 2004/0072749 A1 | 4/2004 | Zochoer et al. |
| 2004/0073026 A1 | 4/2004 | Das et al. |
| 2004/0077875 A1 | 4/2004 | Das et al. |
| 2004/0082664 A1 | 4/2004 | Won et al. |
| 2004/0170626 A1 | 9/2004 | Schuurman et al. |
| 2004/0175786 A1 | 9/2004 | Choi et al. |
| 2004/0204429 A1 | 10/2004 | Yuan |
| 2004/0209801 A1 | 10/2004 | Brand et al. |
| 2004/0229788 A1 | 11/2004 | Tamatani et al. |
| 2005/0009870 A1 | 1/2005 | Sher et al. |
| 2005/0014786 A1 | 1/2005 | Sun et al. |
| 2005/0043233 A1 | 2/2005 | Stefanic et al. |
| 2005/0054659 A1 | 3/2005 | Ellsworth et al. |
| 2005/0080087 A1 | 4/2005 | Pendri et al. |
| 2005/0119269 A1 | 6/2005 | Rao et al. |
| 2005/0143381 A1 | 6/2005 | Yu et al. |
| 2005/0147581 A1 | 7/2005 | Zamiri et al. |
| 2005/0171110 A1 | 8/2005 | Yu et al. |
| 2005/0176028 A1 | 8/2005 | Hofmeister et al. |
| 2005/0191702 A1 | 9/2005 | Mack et al. |
| 2005/0250691 A1 | 11/2005 | Robertson et al. |
| 2006/0002933 A1 | 1/2006 | Bluestone et al. |
| 2006/0057620 A1 | 3/2006 | Krause |
| 2006/0058311 A1 | 3/2006 | Munzert et al. |
| 2006/0062780 A1 | 3/2006 | Zocher et al. |
| 2006/0079563 A1 | 4/2006 | Das et al. |
| 2006/0177896 A1 | 8/2006 | Mach et al. |
| 2006/0183674 A1 | 8/2006 | Brand et al. |
| 2006/0194725 A1 | 8/2006 | Rasmussen et al. |
| 2006/0235201 A1 | 10/2006 | Kischel |
| 2006/0275292 A1 | 12/2006 | Delovitch |
| 2006/0292142 A1 | 12/2006 | Bluestone et al. |
| 2007/0053954 A1 | 3/2007 | Rowe et al. |
| 2007/0065437 A1 | 3/2007 | Elson et al. |
| 2007/0071675 A1 | 3/2007 | Wu et al. |
| 2007/0077246 A1 | 4/2007 | Koenig et al. |
| 2007/0082841 A1 | 4/2007 | Higuchi et al. |
| 2007/0086942 A1 | 4/2007 | Chang et al. |
| 2007/0087971 A1 | 4/2007 | Levetan et al. |
| 2007/0190045 A1 | 8/2007 | Herold et al. |
| 2007/0190052 A1 | 8/2007 | Herold et al. |
| 2007/0249529 A1 | 10/2007 | Hofmeister et al. |
| 2007/0264229 A1 | 11/2007 | Strominger |
| 2007/0292416 A1 | 12/2007 | Rother et al. |
| 2007/0292430 A1 | 12/2007 | Blumenkopf et al. |
| 2008/0009537 A1 | 1/2008 | Sakai |
| 2008/0026378 A1 | 1/2008 | Bottazzo et al. |
| 2008/0044413 A1 | 2/2008 | Hammond et al. |
| 2008/0138339 A1 | 6/2008 | Huang et al. |
| 2008/0171014 A1 | 7/2008 | Wu et al. |
| 2008/0171049 A1 | 7/2008 | Yuan |
| 2008/0207594 A1 | 8/2008 | Mussmann et al. |
| 2008/0213288 A1 | 9/2008 | Michelsen et al. |
| 2008/0248055 A1 | 10/2008 | Robertson et al. |
| 2008/0253991 A1 | 10/2008 | Jevnikar et al. |
| 2008/0254040 A1 | 10/2008 | Stefanic et al. |
| 2008/0287423 A1 | 11/2008 | Mussmann et al. |
| 2009/0041769 A1 | 2/2009 | Peach et al. |
| 2009/0117102 A1 | 5/2009 | Cruz |
| 2009/0142338 A1* | 6/2009 | Levetan ............... A61K 31/454 424/133.1 |
| 2009/0148389 A1 | 6/2009 | Rottiers et al. |
| 2009/0258001 A1 | 10/2009 | Ponath et al. |
| 2009/0269337 A1 | 10/2009 | Brand et al. |
| 2009/0297524 A1 | 12/2009 | Grant et al. |
| 2009/0324609 A1 | 12/2009 | Lodie et al. |
| 2010/0008929 A1 | 1/2010 | van de Winkel et al. |
| 2010/0008932 A1 | 1/2010 | Bensussan et al. |
| 2010/0015142 A1 | 1/2010 | Koenig |
| 2010/0041602 A1 | 2/2010 | Hagerty et al. |
| 2010/0041632 A1 | 2/2010 | Zhang et al. |
| 2010/0047239 A1 | 2/2010 | Wu et al. |
| 2010/0061984 A1 | 3/2010 | Greene et al. |
| 2010/0076178 A1 | 3/2010 | Ghayur et al. |
| 2010/0129357 A1 | 5/2010 | Garcia-Martinez et al. |
| 2010/0129361 A1 | 5/2010 | Ho et al. |
| 2010/0150829 A1 | 6/2010 | Garcia-Martinez et al. |
| 2010/0183554 A1 | 7/2010 | Mach et al. |
| 2010/0183612 A1 | 7/2010 | Peach et al. |
| 2010/0189773 A1 | 7/2010 | Mortimore et al. |
| 2010/0209437 A1 | 8/2010 | elson et al. |
| 2010/0247555 A1 | 9/2010 | Self et al. |
| 2010/0260668 A1 | 10/2010 | Ghayur et al. |
| 2011/0002939 A1 | 1/2011 | Melarkode et al. |
| 2011/0020269 A1 | 1/2011 | Strom et al. |
| 2011/0091372 A1 | 4/2011 | Ghayur et al. |
| 2011/0142761 A1 | 6/2011 | Wu et al. |
| 2011/0165066 A1 | 7/2011 | Wu et al. |
| 2011/0165161 A1 | 7/2011 | Lin et al. |
| 2011/0217302 A1 | 9/2011 | Odegard et al. |
| 2011/0250130 A1 | 10/2011 | Benatuil et al. |
| 2011/0256130 A1 | 10/2011 | Schultz et al. |
| 2011/0262440 A1 | 10/2011 | Zugmaier |
| 2011/0263827 A1 | 10/2011 | Ghayur et al. |
| 2011/0280800 A1 | 11/2011 | Wu et al. |
| 2011/0287533 A1 | 11/2011 | Chang |
| 2011/0300142 A1 | 12/2011 | Salford et al. |
| 2012/0014957 A1 | 1/2012 | Ghayur et al. |
| 2012/0045435 A1 | 2/2012 | Deisher |
| 2012/0052065 A1 | 3/2012 | Peach et al. |
| 2012/0076727 A1 | 3/2012 | McBride et al. |
| 2012/0076753 A1 | 3/2012 | Mandelboim et al. |
| 2012/0088678 A1 | 4/2012 | Albani |
| 2012/0195900 A1 | 8/2012 | Ghayur et al. |
| 2012/0201746 A1 | 8/2012 | Liu et al. |
| 2012/0201781 A1 | 8/2012 | Kamath |
| 2012/0230911 A1 | 9/2012 | Hsieh et al. |
| 2012/0237472 A1 | 9/2012 | Kaplin et al. |
| 2012/0258040 A1 | 10/2012 | Exley et al. |
| 2012/0263722 A1 | 10/2012 | Ghayur et al. |
| 2012/0269826 A1 | 10/2012 | McKee et al. |
| 2012/0321623 A1 | 12/2012 | Suciu-Foca et al. |
| 2013/0004416 A1 | 1/2013 | Wu et al. |
| 2013/0039861 A1 | 2/2013 | Regino et al. |
| 2013/0078238 A1 | 3/2013 | Ilan et al. |
| 2013/0095103 A1 | 4/2013 | Baeuerle et al. |
| 2013/0095121 A1 | 4/2013 | Brennan et al. |
| 2013/0115207 A1 | 5/2013 | Faustman |
| 2013/0129723 A1 | 5/2013 | Blankenship et al. |
| 2013/0171142 A1 | 7/2013 | Brennan et al. |
| 2013/0190233 A1 | 7/2013 | Levetan et al. |
| 2013/0225427 A1 | 8/2013 | Albani |
| 2013/0251671 A1 | 9/2013 | Kaufman |
| 2013/0323247 A1 | 12/2013 | Zugmaier et al. |
| 2014/0066600 A1 | 3/2014 | Chang |
| 2014/0088295 A1 | 3/2014 | Smith et al. |
| 2014/0099313 A1 | 4/2014 | Wu et al. |
| 2014/0099318 A1 | 4/2014 | Huang et al. |
| 2014/0112898 A1 | 4/2014 | Mathis |
| 2014/0120097 A1 | 5/2014 | Levetan |
| 2014/0134171 A1 | 5/2014 | Ghayur et al. |
| 2014/0141020 A1 | 5/2014 | Pages et al. |
| 2014/0147413 A1 | 5/2014 | Chen et al. |
| 2014/0193399 A1 | 7/2014 | Mach et al. |
| 2014/0212425 A1 | 7/2014 | Chang et al. |
| 2014/0220020 A1 | 8/2014 | Wu et al. |
| 2014/0220029 A1 | 8/2014 | Michelsen |
| 2014/0234405 A1 | 8/2014 | Levetan |
| 2014/0235552 A1 | 8/2014 | Levetan |
| 2014/0242077 A1 | 8/2014 | Choi et al. |
| 2014/0242081 A1 | 8/2014 | Hammond et al. |
| 2014/0255956 A1 | 9/2014 | Lipes et al. |
| 2014/0271464 A1 | 9/2014 | Garcia-Martinez et al. |
| 2015/0004167 A1 | 1/2015 | Wu et al. |
| 2015/0010508 A1 | 1/2015 | Levetan et al. |
| 2015/0018360 A1 | 1/2015 | Halse et al. |
| 2015/0023977 A1 | 1/2015 | Fraunhofer et al. |

(56) References Cited

U.S. PATENT DOCUMENTS

| | | |
|---|---|---|
| 2015/0044212 A1 | 2/2015 | Xiao et al. |
| 2015/0050238 A1 | 2/2015 | Kamath |
| 2015/0056167 A1 | 2/2015 | Levetan et al. |
| 2015/0079088 A1 | 3/2015 | Lowman et al. |
| 2015/0079093 A1 | 3/2015 | Stuhler |
| 2015/0086548 A1 | 3/2015 | Levetan |
| 2015/0104452 A1 | 4/2015 | Ghayur et al. |
| 2015/0118252 A1 | 4/2015 | Ho et al. |
| 2015/0140007 A1 | 5/2015 | Wang et al. |
| 2015/0141438 A1* | 5/2015 | Kendall ............ A61P 3/00 514/262.1 |
| 2015/0166661 A1 | 6/2015 | Chen et al. |
| 2015/0174111 A1 | 6/2015 | Levetan |
| 2015/0175699 A1 | 6/2015 | Ellis et al. |
| 2015/0183875 A1 | 7/2015 | Cobbold et al. |
| 2015/0231241 A1 | 8/2015 | Chang et al. |
| 2015/0252110 A1 | 9/2015 | Hansen et al. |
| 2015/0274844 A1 | 10/2015 | Blankenship et al. |
| 2015/0297598 A1 | 10/2015 | Friedman et al. |
| 2015/0299320 A1 | 10/2015 | Exley et al. |
| 2015/0361170 A1 | 12/2015 | Fraunhofer et al. |
| 2016/0039942 A1 | 2/2016 | Cobbold et al. |
| 2016/0046714 A1 | 2/2016 | Koenig et al. |
| 2016/0046730 A1 | 2/2016 | Ghayur et al. |
| 2016/0090416 A1 | 3/2016 | Gunde et al. |
| 2016/0106710 A1 | 4/2016 | Sun et al. |
| 2016/0122436 A1 | 5/2016 | Kufer et al. |
| 2016/0159921 A1 | 6/2016 | D'Angelo et al. |
| 2016/0206682 A1 | 7/2016 | Levetan |
| 2016/0206683 A1 | 7/2016 | Levetan |
| 2016/0213740 A1 | 7/2016 | Levetan |
| 2016/0213741 A1 | 7/2016 | Levetan |
| 2016/0213746 A1 | 7/2016 | Levetan |
| 2016/0215051 A1 | 7/2016 | Sharma et al. |
| 2016/0272703 A1 | 9/2016 | Hsieh et al. |
| 2016/0287622 A1 | 10/2016 | Chang et al. |
| 2016/0289341 A1 | 10/2016 | Wu |
| 2016/0296632 A1 | 10/2016 | Chipman |
| 2016/0311915 A1 | 10/2016 | Pule et al. |
| 2016/0311919 A1 | 10/2016 | Xiao et al. |
| 2016/0317654 A1 | 11/2016 | Noelle et al. |
| 2016/0324798 A1 | 11/2016 | Han et al. |
| 2016/0347850 A1 | 12/2016 | Benatuil et al. |
| 2016/0361360 A1 | 12/2016 | Chang et al. |
| 2017/0015758 A1 | 1/2017 | Hammond et al. |
| 2017/0021017 A1 | 1/2017 | Chang et al. |
| 2017/0022274 A1 | 1/2017 | Chang et al. |
| 2017/0058027 A1 | 3/2017 | Wu et al. |
| 2017/0058043 A1 | 3/2017 | Solman |
| 2017/0073415 A1 | 3/2017 | Urech et al. |
| 2017/0128493 A1 | 5/2017 | Deisher |
| 2017/0137519 A1 | 5/2017 | Huang et al. |
| 2017/0145115 A1 | 5/2017 | Blein et al. |
| 2017/0173117 A1 | 6/2017 | Paulsen et al. |
| 2017/0216218 A1 | 8/2017 | Farokhzad et al. |
| 2017/0218091 A1 | 8/2017 | Ambrosi |
| 2017/0266199 A1 | 9/2017 | Berger et al. |
| 2017/0283446 A1 | 10/2017 | Fan et al. |
| 2017/0304213 A1 | 10/2017 | Shi et al. |
| 2017/0342151 A1 | 11/2017 | Ferrone et al. |
| 2017/0342160 A1 | 11/2017 | Mertens et al. |
| 2017/0362240 A1 | 12/2017 | Allen et al. |
| 2017/0362299 A1 | 12/2017 | Li et al. |
| 2018/0036285 A1 | 2/2018 | Tunac et al. |
| 2018/0057593 A1 | 3/2018 | Dennis |
| 2018/0117152 A1 | 5/2018 | Lee et al. |
| 2018/0134804 A1 | 5/2018 | Scheinberg et al. |
| 2018/0177880 A1 | 6/2018 | Shalibhai |
| 2018/0193477 A1 | 7/2018 | Ng et al. |
| 2018/0237522 A1 | 8/2018 | Snell et al. |
| 2018/0244778 A1 | 8/2018 | Ellis et al. |
| 2018/0251503 A1 | 9/2018 | Ahmed et al. |
| 2018/0273623 A1 | 9/2018 | Cheung et al. |
| 2018/0280507 A1 | 10/2018 | Yu et al. |
| 2018/0291114 A1 | 10/2018 | Ostrand-Rosenberg et al. |
| 2018/0296699 A1 | 10/2018 | Xie |
| 2018/0318230 A1 | 11/2018 | Chopra et al. |
| 2018/0344845 A1 | 12/2018 | Reimann et al. |
| 2018/0346591 A1 | 12/2018 | Soliman |
| 2018/0355064 A1 | 12/2018 | Blein et al. |
| 2019/0004064 A1 | 1/2019 | Chen et al. |
| 2019/0010242 A1 | 1/2019 | Eckelman et al. |
| 2019/0022154 A1 | 1/2019 | Rottiers et al. |
| 2019/0022205 A1 | 2/2019 | Salih et al. |
| 2019/0038733 A1 | 2/2019 | Campana et al. |
| 2019/0046571 A1 | 2/2019 | Campana et al. |
| 2019/0070248 A1 | 3/2019 | Sahin et al. |
| 2019/0077856 A1 | 3/2019 | Scheinberg et al. |
| 2019/0135894 A1 | 5/2019 | Ma et al. |
| 2019/0135918 A1 | 5/2019 | Ollier et al. |
| 2019/0153471 A1 | 5/2019 | Paul et al. |
| 2019/0169296 A1 | 6/2019 | Russell et al. |
| 2019/0170752 A1 | 6/2019 | Luo et al. |
| 2019/0184026 A1 | 6/2019 | Li et al. |
| 2019/0185511 A1 | 6/2019 | Kanne et al. |
| 2019/0194690 A1 | 6/2019 | Champion et al. |
| 2019/0233534 A1 | 8/2019 | Mehlin et al. |
| 2019/0233536 A1 | 8/2019 | Champion et al. |
| 2019/0248924 A1 | 8/2019 | Wu |
| 2019/0276541 A1 | 9/2019 | Eavarone et al. |
| 2019/0284296 A1 | 9/2019 | Stuhler |
| 2019/0284299 A1 | 9/2019 | Liu et al. |
| 2019/0292551 A1 | 9/2019 | Rottiers et al. |
| 2019/0300526 A1 | 10/2019 | Fan et al. |
| 2019/0300609 A1 | 10/2019 | Zugmaier et al. |
| 2019/0314417 A1 | 10/2019 | Wobma et al. |
| 2019/0330362 A1 | 10/2019 | Moffat et al. |
| 2019/0343964 A1 | 11/2019 | Akiyama et al. |
| 2019/0351056 A1 | 11/2019 | Christen et al. |
| 2019/0352421 A1 | 11/2019 | Adams et al. |
| 2019/0359732 A1 | 11/2019 | Cheung et al. |
| 2019/0382497 A1 | 12/2019 | Poirier et al. |
| 2020/0023076 A1 | 1/2020 | Fotin-Mleczek et al. |
| 2020/0024363 A1 | 1/2020 | Teran et al. |
| 2020/0040056 A1 | 2/2020 | DiPersio et al. |
| 2020/0040099 A1 | 2/2020 | Kufer et al. |
| 2020/0048356 A1 | 2/2020 | Liu |
| 2020/0071397 A1 | 3/2020 | DiPersio et al. |
| 2020/0079854 A1 | 3/2020 | Hsiue et al. |
| 2020/0087412 A1 | 3/2020 | Fang et al. |
| 2020/0113940 A1 | 4/2020 | Maus et al. |
| 2020/0157218 A1 | 5/2020 | Nathwani et al. |
| 2020/0157249 A1 | 5/2020 | Wu |
| 2020/0181260 A1 | 6/2020 | Davila |
| 2020/0181264 A1 | 6/2020 | Rossi et al. |
| 2020/0181288 A1 | 6/2020 | Jang et al. |
| 2020/0199169 A1 | 6/2020 | Leong et al. |
| 2020/0199232 A1 | 6/2020 | Qin et al. |
| 2020/0199248 A1 | 6/2020 | Cheung et al. |
| 2020/0206145 A1 | 7/2020 | Shi et al. |
| 2020/0207851 A1 | 7/2020 | Chen et al. |
| 2020/0216859 A1 | 7/2020 | Champion et al. |
| 2020/0239571 A1 | 7/2020 | Bramson et al. |
| 2020/0261574 A1 | 8/2020 | Reimann et al. |
| 2020/0281976 A1 | 9/2020 | Zeng et al. |
| 2020/0308541 A1 | 10/2020 | Ma et al. |
| 2020/0317809 A1 | 10/2020 | Li |
| 2020/0339679 A1 | 10/2020 | Sirianni et al. |
| 2020/0339686 A1 | 10/2020 | Sato et al. |
| 2020/0384107 A1 | 12/2020 | Yu et al. |
| 2020/0399370 A1 | 12/2020 | Sahin et al. |
| 2020/0407452 A1 | 12/2020 | Michieli |
| 2021/0000957 A1 | 1/2021 | Shailubhai |
| 2021/0009596 A1 | 1/2021 | Fan et al. |
| 2021/0009691 A1 | 1/2021 | Mach et al. |
| 2021/0024639 A1 | 1/2021 | Michieli |
| 2021/0032333 A1 | 2/2021 | Leon et al. |
| 2021/0038646 A1 | 2/2021 | Maus et al. |
| 2021/0046112 A1 | 2/2021 | Campana et al. |
| 2021/0052612 A1 | 2/2021 | Fan et al. |
| 2021/0085735 A1 | 3/2021 | Finer et al. |
| 2021/0087267 A1 | 3/2021 | Miano et al. |
| 2021/0107985 A1 | 4/2021 | Schuurman et al. |
| 2021/0108213 A1 | 4/2021 | Rashid et al. |

(56) References Cited

U.S. PATENT DOCUMENTS

| | | | |
|---|---|---|---|
| 2021/0113519 A1 | 4/2021 | Whitehead et al. |
| 2021/0113550 A1 | 4/2021 | Khleif et al. |
| 2021/0113709 A1 | 4/2021 | Demetriou et al. |
| 2021/0130464 A1 | 5/2021 | Leon et al. |
| 2021/0139577 A1 | 5/2021 | Dillon et al. |
| 2021/0139851 A1 | 5/2021 | Chuang et al. |
| 2021/0154247 A1 | 5/2021 | Rottiers et al. |
| 2021/0155713 A1 | 5/2021 | Didonato et al. |
| 2021/0163620 A1 | 6/2021 | Granda et al. |
| 2021/0171661 A1 | 6/2021 | Blein et al. |
| 2021/0177755 A1 | 6/2021 | Dumontet et al. |
| 2021/0180072 A1 | 6/2021 | Rottiers et al. |
| 2021/0188983 A1 | 6/2021 | Robert et al. |
| 2021/0198368 A1 | 7/2021 | Daley et al. |
| 2021/0205248 A1 | 7/2021 | Kaufman et al. |
| 2021/0206853 A1 | 7/2021 | Lindhofer et al. |
| 2021/0214440 A1 | 7/2021 | Ganesan et al. |
| 2021/0214458 A1 | 7/2021 | Liu et al. |
| 2021/0236466 A1 | 8/2021 | Roush et al. |
| 2021/0238291 A1 | 8/2021 | Lowman et al. |
| 2021/0238607 A1 | 8/2021 | Fierabracci |
| 2021/0244815 A1 | 8/2021 | Lee et al. |
| 2021/0246211 A1 | 8/2021 | Goldberg et al. |
| 2021/0251954 A1 | 8/2021 | Sun et al. |
| 2021/0253636 A1 | 8/2021 | Yu et al. |
| 2021/0260173 A1 | 8/2021 | Kjellman et al. |
| 2021/0261645 A1 | 8/2021 | Huang et al. |
| 2021/0261646 A1 | 8/2021 | McGinness et al. |
| 2021/0261649 A1 | 8/2021 | Parry et al. |
| 2021/0269525 A1 | 8/2021 | Parry et al. |
| 2021/0269841 A1 | 8/2021 | Parry et al. |
| 2021/0277127 A1 | 9/2021 | Zhang et al. |
| 2021/0284746 A1 | 9/2021 | Liu et al. |
| 2021/0292423 A1 | 9/2021 | Albrecht et al. |
| 2021/0301015 A1 | 9/2021 | Tseng |
| 2021/0309750 A1 | 10/2021 | Sampson et al. |
| 2021/0324079 A1 | 10/2021 | Cheung et al. |
| 2021/0332134 A1 | 10/2021 | Shibayama et al. |
| 2021/0332334 A1 | 10/2021 | McGinness et al. |
| 2021/0338836 A1 | 11/2021 | Yu et al. |
| 2021/0340219 A1 | 11/2021 | McGinness et al. |
| 2021/0348191 A1 | 11/2021 | Pule et al. |
| 2021/0349094 A1 | 11/2021 | Vasu |
| 2021/0353751 A1 | 11/2021 | Kaufman et al. |
| 2021/0363180 A1 | 11/2021 | Hoang et al. |
| 2021/0363270 A1 | 11/2021 | Park et al. |
| 2021/0371927 A1 | 12/2021 | Gysemans et al. |
| 2021/0379046 A1 | 12/2021 | Scheinberg et al. |
| 2021/0382053 A1 | 12/2021 | Vasiljeva et al. |
| 2021/0386680 A1 | 12/2021 | Cui et al. |
| 2021/0388017 A1 | 12/2021 | Park et al. |
| 2021/0388388 A1 | 12/2021 | Song et al. |
| 2021/0393795 A1 | 12/2021 | Park et al. |
| 2021/0395339 A1 | 12/2021 | Alitalo et al. |
| 2021/0402005 A1 | 12/2021 | Markovic et al. |
| 2022/0002398 A1 | 1/2022 | Thiele et al. |
| 2022/0002407 A1 | 1/2022 | Li et al. |
| 2022/0002408 A1 | 1/2022 | Yuan et al. |
| 2022/0002431 A1 | 1/2022 | Li et al. |
| 2022/0008533 A1 | 1/2022 | Shailubhai |
| 2022/0033427 A1 | 2/2022 | Lourenco et al. |
| 2022/0034903 A1 | 2/2022 | Chen et al. |
| 2022/0041720 A1 | 2/2022 | Leon et al. |
| 2022/0041721 A1 | 2/2022 | Zhang et al. |
| 2022/0041724 A1 | 2/2022 | Twitty et al. |
| 2022/0048961 A1 | 2/2022 | Crook et al. |
| 2022/0056132 A1 | 2/2022 | Qin et al. |
| 2022/0057398 A1 | 2/2022 | Sarvetnick et al. |
| 2022/0073640 A1 | 3/2022 | Moffat et al. |
| 2022/0088196 A1 | 3/2022 | Bauerle et al. |
| 2022/0098307 A1 | 3/2022 | Zhang et al. |
| 2022/0098324 A1 | 3/2022 | Weiner et al. |
| 2022/0098329 A1 | 3/2022 | Santich et al. |
| 2022/0105193 A1 | 4/2022 | Li et al. |
| 2022/0118104 A1 | 4/2022 | Park et al. |
| 2022/0119478 A1 | 4/2022 | Spear et al. |
| 2022/0119549 A1 | 4/2022 | Zhang et al. |
| 2022/0125941 A1 | 4/2022 | Ban et al. |

FOREIGN PATENT DOCUMENTS

| | | |
|---|---|---|
| EP | 1687066 B1 | 8/2006 |
| EP | 1691833 B1 | 8/2006 |
| EP | 1753783 B1 | 2/2007 |
| EP | 1697370 B1 | 4/2007 |
| EP | 1697371 B1 | 4/2007 |
| EP | 1397153 B1 | 4/2008 |
| EP | 1686130 B1 | 2/2009 |
| EP | 2037961 B1 | 3/2009 |
| EP | 1379270 B1 | 9/2009 |
| EP | 1337527 B1 | 10/2009 |
| EP | 1837031 B1 | 10/2009 |
| EP | 2193142 B1 | 6/2010 |
| EP | 1716178 B1 | 8/2010 |
| EP | 1827492 B1 | 8/2010 |
| EP | 1697421 B1 | 9/2010 |
| EP | 1673398 B1 | 12/2010 |
| EP | 2270051 B1 | 1/2011 |
| EP | 1451192 B1 | 2/2011 |
| EP | 1798240 B1 | 4/2011 |
| EP | 2397189 B1 | 12/2011 |
| EP | 1879591 B1 | 1/2012 |
| EP | 2288372 B1 | 2/2012 |
| EP | 2096120 B1 | 3/2012 |
| EP | 1578397 B1 | 12/2012 |
| EP | 2119450 B1 | 2/2013 |
| EP | 1973573 B1 | 5/2013 |
| EP | 1797126 B1 | 10/2013 |
| EP | 1613628 B1 | 11/2013 |
| EP | 1740946 B1 | 11/2013 |
| EP | 2164500 B1 | 12/2013 |
| EP | 2408468 B1 | 4/2014 |
| EP | 2714733 B1 | 4/2014 |
| EP | 2755999 B1 | 7/2014 |
| EP | 1976886 B1 | 12/2014 |
| EP | 2814963 B1 | 12/2014 |
| EP | 2344539 B1 | 2/2015 |
| EP | 2892924 B1 | 7/2015 |
| EP | 2342227 B1 | 10/2015 |
| EP | 2551347 B1 | 11/2015 |
| EP | 2295066 B1 | 4/2016 |
| EP | 3024484 B1 | 6/2016 |
| EP | 1957100 B1 | 7/2016 |
| EP | 1976880 B1 | 7/2016 |
| EP | 2292664 B1 | 11/2016 |
| EP | 2029145 B1 | 1/2017 |
| EP | 3464352 B1 | 5/2017 |
| EP | 2066174 B1 | 11/2017 |
| EP | 1629013 B1 | 1/2018 |
| EP | 2854845 B1 | 3/2018 |
| EP | 2793923 B1 | 5/2018 |
| EP | 3024851 B1 | 5/2018 |
| EP | 2835379 B1 | 7/2018 |
| EP | 2764362 B1 | 9/2018 |
| EP | 2878308 B1 | 10/2018 |
| EP | 1629012 B1 | 11/2018 |
| EP | 3129483 B1 | 11/2018 |
| EP | 2968545 B1 | 3/2019 |
| EP | 2982696 B1 | 3/2019 |
| EP | 3330293 B1 | 7/2019 |
| EP | 3087095 B1 | 8/2019 |
| EP | 2993186 B1 | 9/2019 |
| EP | 2793912 B1 | 3/2020 |
| EP | 3044234 B1 | 3/2020 |
| EP | 3083689 B1 | 5/2020 |
| EP | 3186277 B1 | 10/2020 |
| EP | 3227297 B1 | 1/2021 |
| EP | 3791931 A1 | 3/2021 |
| EP | 3318565 B1 | 4/2021 |
| EP | 3402494 B1 | 4/2021 |
| EP | 3402499 B1 | 4/2021 |
| EP | 2819701 B2 | 6/2021 |
| EP | 3310811 B1 | 6/2021 |
| EP | 3504316 B1 | 6/2021 |

(56) References Cited

FOREIGN PATENT DOCUMENTS

| | | |
|---|---|---|
| EP | 2242504 B1 | 7/2021 |
| EP | 3268391 B1 | 8/2021 |
| EP | 2742953 B1 | 9/2021 |
| EP | 3297672 B1 | 9/2021 |
| EP | 3389682 B1 | 11/2021 |
| EP | 3439658 B1 | 11/2021 |
| EP | 3194439 B1 | 1/2022 |
| EP | 3230311 B1 | 1/2022 |
| EP | 3703718 B1 | 1/2022 |
| WO | WO2007147090 A2 | 12/2007 |
| WO | WO2015073833 | 5/2015 |
| WO | WO2017125897 A1 | 7/2017 |
| WO | WO2017193956 A1 | 11/2017 |
| WO | WO2018037416 A1 | 3/2018 |
| WO | WO2018068652 A1 | 4/2018 |
| WO | WO2018120842 A1 | 7/2018 |
| WO | WO2018177371 A1 | 10/2018 |
| WO | WO2018178123 A1 | 10/2018 |
| WO | WO2018237192 A1 | 12/2018 |
| WO | 2019050465 A1 | 3/2019 |
| WO | WO2019091384 A1 | 5/2019 |
| WO | WO2019094669 A2 | 5/2019 |
| WO | WO2019126133 A1 | 6/2019 |
| WO | WO2019133847 A1 | 7/2019 |
| WO | WO2019185864 A1 | 10/2019 |
| WO | WO2019195535 A1 | 10/2019 |
| WO | WO2019204434 A1 | 10/2019 |
| WO | WO2019215772 A1 | 11/2019 |
| WO | WO2019219913 A1 | 11/2019 |
| WO | WO2019222082 A1 | 11/2019 |
| WO | WO2019226894 A1 | 11/2019 |
| WO | WO2019234241 A1 | 12/2019 |
| WO | 2020001344 A1 | 1/2020 |
| WO | 2020006486 A1 | 1/2020 |
| WO | WO2020014097 A1 | 1/2020 |
| WO | WO2020028444 A1 | 2/2020 |
| WO | 2020047176 A1 | 3/2020 |
| WO | 2020056037 A1 | 3/2020 |
| WO | WO2020053301 A1 | 3/2020 |
| WO | WO2020056170 A1 | 3/2020 |
| WO | WO2020081885 A1 | 4/2020 |
| WO | WO2020081886 A1 | 4/2020 |
| WO | WO2020086423 A1 | 4/2020 |
| WO | WO2020089396 A2 | 5/2020 |
| WO | WO2020092743 A2 | 5/2020 |
| WO | 2020112987 A1 | 6/2020 |
| WO | WO2020113164 A1 | 6/2020 |
| WO | WO2020123806 A1 | 6/2020 |
| WO | WO2020124032 A1 | 6/2020 |
| WO | 2020168555 A1 | 8/2020 |
| WO | WO2020160310 A1 | 8/2020 |
| WO | WO2020168554 A1 | 8/2020 |
| WO | WO2020172259 A1 | 8/2020 |
| WO | 2020190217 A2 | 9/2020 |
| WO | WO2020185763 A1 | 9/2020 |
| WO | WO2020186974 A1 | 9/2020 |
| WO | WO2020191344 A1 | 9/2020 |
| WO | 2020206063 A1 | 10/2020 |
| WO | WO2020191486 A1 | 10/2020 |
| WO | WO2020210232 A1 | 10/2020 |
| WO | WO2020210843 A2 | 10/2020 |
| WO | WO2020214928 A1 | 10/2020 |
| WO | WO2020222010 A1 | 11/2020 |
| WO | WO2020222011 A1 | 11/2020 |
| WO | WO2020223279 A1 | 11/2020 |
| WO | WO2020226854 A2 | 11/2020 |
| WO | WO2020227538 A1 | 11/2020 |
| WO | WO2020229553 A1 | 11/2020 |
| WO | 2020247867 A1 | 12/2020 |
| WO | 2020247871 A2 | 12/2020 |
| WO | WO2020247385 A1 | 12/2020 |
| WO | WO2021001458 A1 | 1/2021 |
| WO | WO2021016316 A1 | 1/2021 |
| WO | WO2021038975 A1 | 3/2021 |
| WO | WO2021041725 A1 | 3/2021 |
| WO | WO2021041958 A1 | 3/2021 |
| WO | WO2021044008 A1 | 3/2021 |
| WO | WO2021048724 A1 | 3/2021 |
| WO | WO2021060638 A1 | 4/2021 |
| WO | WO2021064069 A1 | 4/2021 |
| WO | WO2021071319 A1 | 4/2021 |
| WO | WO2021072264 A1 | 4/2021 |
| WO | WO2021090321 A1 | 5/2021 |
| WO | WO2021092672 A1 | 5/2021 |
| WO | WO2021110935 A1 | 6/2021 |
| WO | WO2021111185 A1 | 6/2021 |
| WO | WO2021116398 A1 | 6/2021 |
| WO | WO2021119585 A1 | 6/2021 |
| WO | WO2021127489 A1 | 6/2021 |
| WO | WO2021130492 A1 | 7/2021 |
| WO | WO2021138600 A1 | 7/2021 |
| WO | WO2021144315 A1 | 7/2021 |
| WO | WO2021146328 A1 | 7/2021 |
| WO | WO2021155071 A1 | 8/2021 |
| WO | WO2021165248 A1 | 8/2021 |
| WO | WO2021173783 A1 | 9/2021 |
| WO | WO2021183839 A2 | 9/2021 |
| WO | WO2021188590 A2 | 9/2021 |
| WO | WO2021195067 A1 | 9/2021 |
| WO | WO2021202726 A2 | 10/2021 |
| WO | WO2021202770 A2 | 10/2021 |
| WO | WO2021207828 A1 | 10/2021 |
| WO | WO2021213421 A1 | 10/2021 |
| WO | WO2021216460 A1 | 10/2021 |
| WO | WO2021216972 A1 | 10/2021 |
| WO | WO2021222746 A2 | 11/2021 |
| WO | WO2021222861 A1 | 11/2021 |
| WO | WO2021243206 A1 | 12/2021 |
| WO | WO2021252780 A2 | 12/2021 |
| WO | WO2021254574 A2 | 12/2021 |
| WO | WO2022013872 A1 | 1/2022 |
| WO | WO2022018262 A1 | 1/2022 |
| WO | WO2022026439 A2 | 2/2022 |
| WO | WO2022026939 A2 | 2/2022 |
| WO | WO2022027039 A1 | 2/2022 |
| WO | WO2022029438 A1 | 2/2022 |
| WO | WO2022032004 A2 | 2/2022 |
| WO | WO2022033419 A2 | 2/2022 |
| WO | WO2022035888 A2 | 2/2022 |
| WO | WO2022036495 A1 | 2/2022 |
| WO | WO2022037520 A1 | 2/2022 |
| WO | WO2022038365 A2 | 2/2022 |
| WO | WO2022040429 A2 | 2/2022 |
| WO | WO2022040603 A2 | 2/2022 |
| WO | WO2022045247 A1 | 3/2022 |
| WO | WO2022053036 A1 | 3/2022 |
| WO | WO2022058298 A1 | 3/2022 |
| WO | WO2022060832 A1 | 3/2022 |
| WO | WO2022063302 A1 | 3/2022 |
| WO | WO2022067224 A1 | 3/2022 |
| WO | WO2022076898 A1 | 4/2022 |
| WO | WO2022083853 A1 | 4/2022 |
| WO | WO2022087149 A2 | 4/2022 |

OTHER PUBLICATIONS

Diabetes Study Group, "Effects of Insulin in Relatives of Patients with Type 1 Diabetes Mellitus" New England Journal of Medicine, vol. 346, No. 22, pp. 1685-1691, May 30, 2002.

Espluges et al., "Control of TH17 Cells Occurs in the Small Intestine" Nature, vol. 475, pp. 514-520, Jul. 28, 2011.

Gale et al., "European Nicotinamide Diabetes Intervention Trial (ENDIT): A Randomised Controlled Trial of Intervention Before the Onset of Type 1 Diabetes" Lancet, vol. 363, pp. 925-931, Mar. 20, 2004.

Greenbaum et al., "Fall in C-Peptide During First 2 Years from Diagnosis: Evidence of at Least Two Distinct Phases from Composite TrialNet Data" Diabetes, vol. 61, pp. 2066-2073, Aug. 2012.

Hagopian et al., "Teplizumab Preserves C-Peptide in Recent-Onset Type 1 Diabetes—Two-Year Results from the Randomized, Placebo-Controlled Protege Trial" Diabetes, vol. 62, pp. 3901-3908, Nov. 2013.

(56) References Cited

OTHER PUBLICATIONS

Herold et al, "Anti-CD3 Monoclonal Antibody in New-Onset Type 1 Diabetes Mellitus" New England Journal of Medicine, vol. 346, pp. 1692-1698, May 30, 2002.
Herold et al., "A Single Course of Anti-CD3 Monoclonal Antibody hOKT3γ1 (Ala-Ala) Results in Improvement in C-Peptide Responses and Clinical Parameters for at Least 2 Years after Onset of Type 1 Diabetes" Diabetes, vol. 54, pp. 1763-1769, Jun. 2005.
Herold et al., Activation of Human T Cells by FcR Nonbinding Anti-CD3 mAb, hOKT3 gamma1 (Ala-Ala), Journal of Clinical Investigation, vol. 111, No. 3, pp. 409-418, Feb. 2003.
Herold et al., "An Anti-CD3 Antibody, Teplizumab, in Relatives at Risk for Type 1 Diabetes" The New England Journal of Medicine, vol. 381, No. 7, pp. 603-613, Aug. 15, 2019.
Herold et al., "Beta Cell Death and Dysfunction During Type 1 Diabetes Development in At-Risk Individuals" Journal of Clinical Investigation, vol. 125, No. 3, pp. 1163-1173, Mar. 2015.
Herold et al., "Teplizumab (Anti-CD3 mAb) Treatment Preserves C-Peptide Responses in Patients With New-Onset Type 1 Diabetes in a Randomized Control Trial" Diabetes, vol. 62, pp. 3766-3774, Nov. 2013.
Herold et al., "Teplizumab Treatment May Improve C-Peptide Responses in Participants with Type 1 Diabetes after the New-Onset Period: A Randomised Controlled Trial", Diabetologia, vol. 6, pp. 391-400, Feb. 2013.
Hippich et al., "Genetic Contribution to the Divergence in Type 1 Diabetes Risk Between Children From the General Population and Children from Affected Families" Diabetes, vol. 68,pp. 847-857, Apr. 2019.
Insel et al., "Staging Presymptomatic Type 1 Diabetes: A Scientific Statement of JDRF, the Endocrine Society, and the American Diabetes Association" Diabetes Care, vol. 38, pp. 1964-1974, Oct. 2015.
Keymeulen et al., "Insulin Needs After CD3-Antibody Therapy in New-Onset Type 1 Diabetes" Lancet Diabetes Endocrinol, vol. 7, pp. 52-64, 2019.
Kuhn et al., "Therapeutic Anti-CD3 Monoclonal Antibodies: From Bench to Bedside" Immunotherapy, vol. 8, No. 8, pp. 889-906, May 10, 2016.
Lan et al., Discrete Sequential Boundaries for Clinical Trials, Biometrika, vol. 70, No. 3, pp. 659-663, Dec. 1983.
Livingstone et al., "Estimated Life Expectancy in a Scottish Cohort with Type 1 Diabetes" JAMA, vol. 313, No. 1, pp. 37-44, Jan. 6, 2015.
Long et al., "Partial Exhaustion of CD8 T Cells and Clinical Response to Teplizumab in New-Onset Type 1 Diabetes" Science Immunology, vol. 1, No. 5, pp. 1-23, Nov. 18, 2016.
Mantel et al., "Evaluation of Suvival Data and Two New Rank Order Statistics Arising in its Consideration" Cancer Chemotherapy Reports, vol. 50, No. 3, pp. 163-170, Mar. 1966.
Menke et al., "The Prevalence of Type 1 Diabetes in the United States" Epidemiology, vol. 24, No. 5, pp. 773-774, Sep. 2013.
Miller et al., "Current State of Type 1 Diabetes Treatment in the United States" Diabetes Care, vol. 38, pp. 971-978, Jun. 2015.
Perdigoto et al., "Treatment of Type 1 Diabetes with Teplizumab: Clinical and Immunological Follow-Up after 7 Years from Diagnosis" Diabetologia, vol. 62, No. 4, pp. 655-664, Apr. 2019.
Rawshani et al., "Excess Mortality and Cardiovascular Disease in Young Adults with Type 1 Diabetes in Relation to Age at Onset: a Nationwide, Register-Based Cohort Study" Lancet vol. 392, pp. 477-486, Aug. 11, 2018.
Schoenfeld, "Sample-size Formula for the Proportional-Hazards Regression Model" Biometrics, vol. 39, No. 2, pp. 499-503, Jun. 1983.
Sherry et al., "Teplizumab for Treatment of Type 1 Diabetes (Protégé Study): 1-Year Results from a Randomised, Placebo-Controlled Trial" Lancet, vol. 378, Issue 9790, pp. 487-497, Aug. 6, 2011.
Therneau et al., "Modeling Survival Data: Extending the Cox Model". Statistics for Biology and Health. Springer, New York, NY pp. 39-77, 2000. https://doi.org/10.1007/978-1-4757-3294-8_3.
Tooley et al., "Changes in T-Cell Subsets Identify Responders to FcR Non-Binding Anti-CD3 mAb (teplizumab) in Patients with Type 1 Diabetes" European Journal of Immunology, vol. 46, pp. 230-241, Jan. 2016.
Waldron-Lynch et al., "Teplizumab Induces Human Gut-Tropic Regulatory Cells in Humanized Mice and Patients" Science Translational Medicine, vol. 4, Issue 118, pp. 1-29, Jan. 25, 2012.
Wherrett et al., "Defining Pathways for Development of Disease-Modifying Therapies in Children With Type 1 Diabetes: A Consensus Report" Diabetes Care, vol. 38, pp. 1975-1985, Oct. 2015.
Wherry, "T Cell Exhaustion" Nature Immunology, vol. 12, No. 6, pp. 492-498, Jun. 2011.
Wherry et al., "Molecular Signature of CD8+ T Cell Exhaustion During Chronic Viral Infection" Immunity, vol. 27, pp. 670-684, Oct. 2007.
International Search Report in International Patent Application No. PCT/US2020/032891 dated Aug. 26, 2020.
International Preliminary Report on Patentability in International Patent Application No. PCT/US2020/032891 dated Jan. 12, 2021.
Dayan et al., "Changing the Landscape for Type 1 Diabetes: The First Step to Prevention" Lancet, vol. 394, pp. 1286-1296, Oct. 5, 2019.
Skowera et al., "beta-Cell-Specific CD8 T Cell Phenotype in Type 1 Diabetes Reflects Chronic Autoantigen Exposure", Diabetes, vol. 64, No. 3, pp. 916-926, Mar. 2015.
Anonymous: "Anti-CD3 Prevention ANTI-CD3 Mab (Teplizumab) for Prevention of Diabetes in Relatives at-risk for type 1 Diabetes Mellitus (Protocol Tn-10", Type 1 Diabetes TrialNet, Protocol Version Jun. 25, 2014, https://clinicaltrials.gov/ProvidedDocs/61/NCT01030861/Prot_000.
Mannering et al., "The Case for an Autoimmune Aetiology of Type 1 Diabetes", Clinical and Experimental Immunology, Wiley-Blackwell Publishing Ltd., GB, vol. 183, No. 1, pp. 8-15, Oct. 21, 2015.
Noble et al., "Genetics of the HLA Region in the Prediction of Type 1 Diabetes", Current Diabetes Reports, Current Science, Inc., vol. 11, No. 6, pp. 533-542, Sep. 13, 2011.
Wherrett et al., "Prevention of Type 1 Diabetes" Endocrinology and Metabolism Clinics of North America, vol. 38, No. 4, pp. 777-792, Dec. 1, 2009.
Wu et al., "Risk Factors and Primary Prevention Trials for Type 1 Diabetes", International Journal of Biological Sciences, vol. 9, No. 7, pp. 666-679, Jul. 18, 2013.

\* cited by examiner

Figure 2B

| Year | No. of T1D* | | Chi-square Test† | Hazard Ratio (95%CI)† | |
|---|---|---|---|---|---|
| | Teplizumab (%) | Placebo (%) | | Cumulative | Interval |
| 1 | 3 (6.8%) | 14 (43.8%) | 15.9 | 0.129 (0.0482, 0.343) | 0.129 (0.0482, 0.343) |
| 2 | 8 (18.2%) | 2 (6.3%) | 7.55 | 0.372 (0.169, 0.82) | 1.8 (0.473, 6.88) |
| 3 | 3 (6.8%) | 3 (9.4%) | 7.77 | 0.404 (0.198, 0.825) | 0.58 (0.11, 3.05) |
| 4 | 3 (6.8%) | 2 (6.3%) | 7.05 | 0.447 (0.23, 0.869) | 0.864 (0.14, 5.33) |
| 5 | 2 (4.5%) | 2 (6.3%) | 8.24 | 0.439 (0.233, 0.828) | 0.359 (0.039, 3.32) |
| Total | 19 (43.2%) | 23 (71.9%) | 7.77€ | 0.419 (0.228, 0.772)€ | -- |

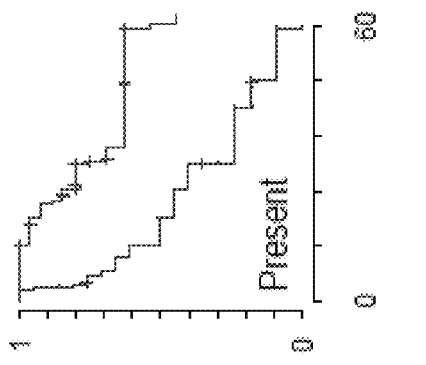
Figure 3E
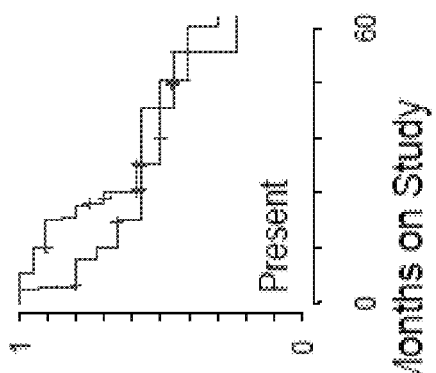
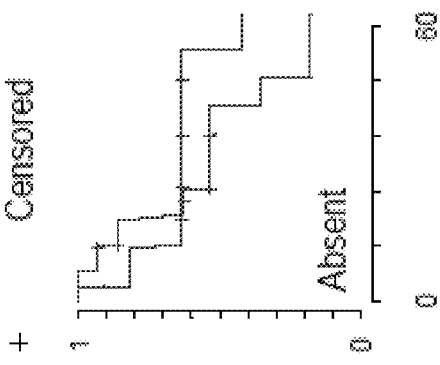
Figure 3D
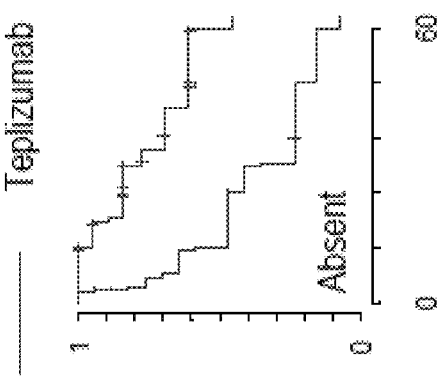
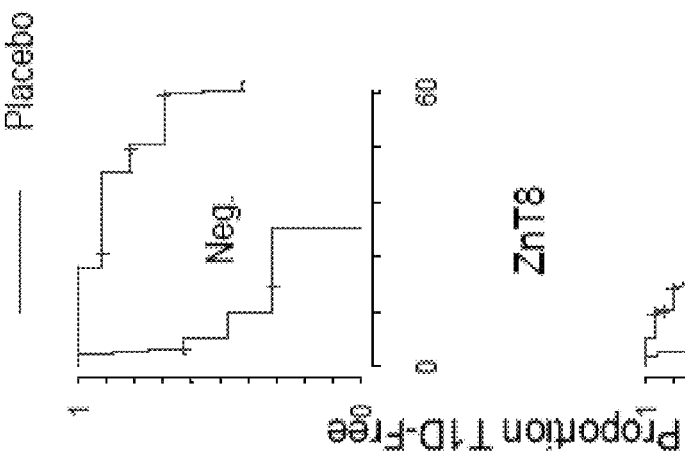
Figure 3C

Figure 4

| Marker | Format | Clone | Vendor |
|---|---|---|---|
| CD56 | BUV395 | NCAM16.2 | Becton Dickinson |
| CD45RA | BUV737 | HI100 | Becton Dickinson |
| Ki67 | BV421 | Ki-67 | BioLegend |
| CCR7 | BV510 | G043H7 | BioLegend |
| CD3 | BV605 | OKT3 | BioLegend |
| PD1 | BV650 | EH12.2H7 | BioLegend |
| CD127 | BV711 | A019D5 | BioLegend |
| CD45RO | BV786 | UCHL1 | Becton Dickinson |
| CD4 | BB515 | RPA-T4 | Becton Dickinson |
| Eomes | PE | WD1928 | eBiosciences |
| FoxP3 | PE-CF594 | 259D/C7 | Becton Dickinson |
| KLRG1 | PE-Vio770 | REA261 | Miltenyi |
| TIGIT | APC | MBSA43 | eBiosciences |
| CD8 | Ax700 | SK1 | BioLegend |
| CD57 | APC-Vio770 | REA769 | Miltenyi |
| Live/dead | BUV496 | NA | Becton Dickinson |

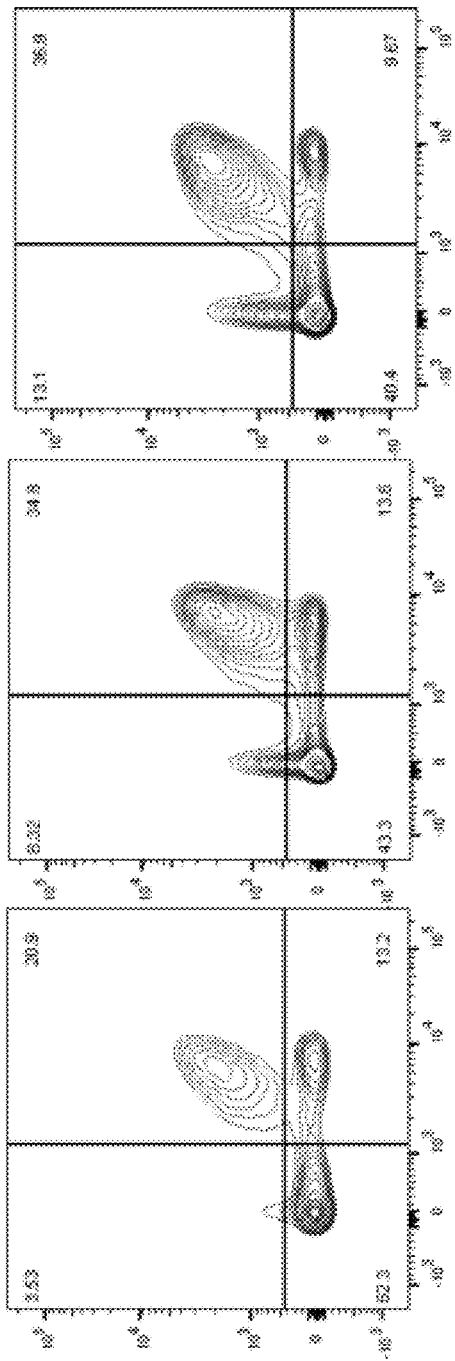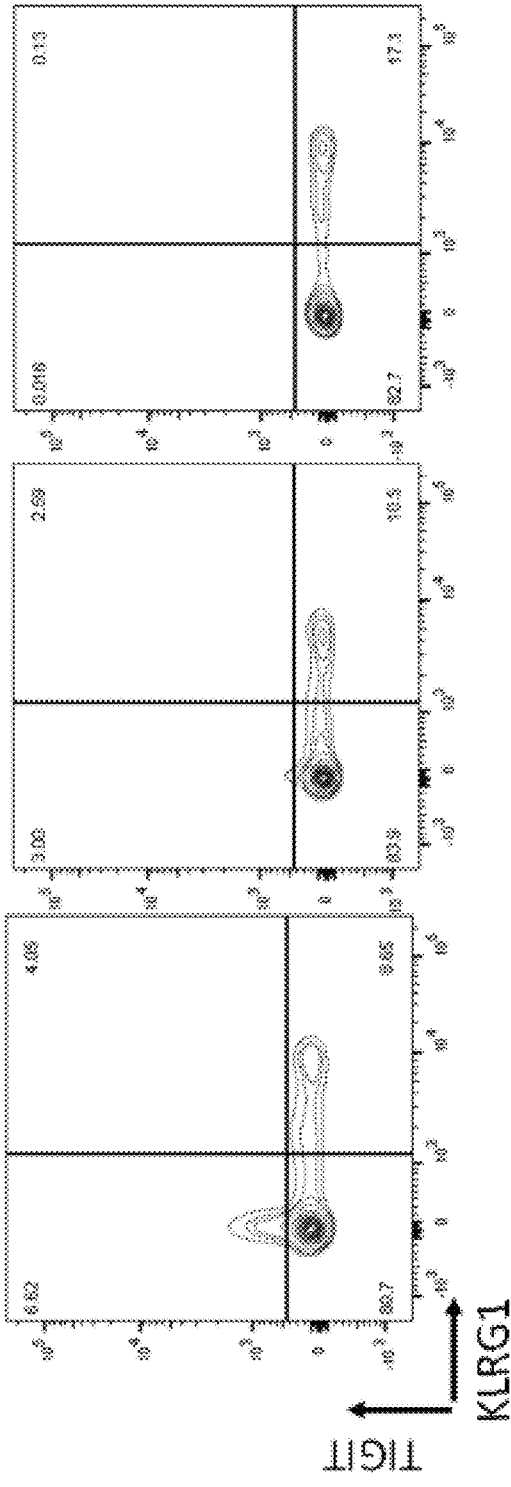
Figure 6

METHODS AND COMPOSITIONS FOR PREVENTING TYPE 1 DIABETES

CROSS REFERENCE TO RELATED APPLICATIONS

This application claims priority to and the benefit of U.S. Provisional Application No. 62/847,466 filed May 14, 2019, the entire disclosure of which is incorporated herein by reference.

GOVERNMENT SUPPORT

This invention was made with United States Government support under grant numbers 5U01DK061041, 5U01DK061037, 5U01DK085499, 2U01DK106993, U01DK085466, R01 DK057846 awarded by National Institutes of Health, and grant numbers HHSN267200800019C, 1UC4DK097835, 1UC4DK117009 awarded by National Institute of Diabetes and Digestive and Kidney Diseases. The United States Government has certain rights in the invention.

SEQUENCE LISTING

The ASCII text file submitted on May 14, 2020 via EFS-Web, entitled "010701seq.txt" created on May 14, 2020, having a size of 6,083 bytes, is incorporated herein by reference in its entirety.

FIELD

The present disclosure relates in general to compositions and methods of preventing or delaying the onset of clinical type 1 diabetes (T1D) in subjects at risk, and more particularly the use of anti-CD3 antibodies.

BACKGROUND

Type 1 diabetes (T1D) is caused by the autoimmune destruction of insulin producing beta cells in the islets of Langerhans leading to dependence on exogeneous insulin injections for survival. Approximately 1.6 million Americans have Type 1 diabetes, and after asthma, it remains one of the most common diseases of childhood[1]. Despite improvements in care most affected individuals with T1D are not able to consistently achieve desired glycemic targets[2]. For individuals with type 1 diabetes, there are persisting concerns for increased risk of both morbidity and mortality. Two recent studies noted loss of 17.7 life-years for children diagnosed before age 10, and 11 and 13 life-years lost for adult-diagnosed Scottish men and women respectively[3,4].

In genetically susceptible individuals, T1D progresses through asymptomatic stages prior to overt hyperglycemia, characterized first by the appearance of autoantibodies (Stage 1) and then dysglycemia (Stage 2). In Stage 2, metabolic responses to a glucose load are impaired but other metabolic indices, for example glycosylated hemoglobin, are normal and insulin treatment is not needed[5]. These immunologic and metabolic features identify individuals who are at high-risk for development of clinical disease with overt hyperglycemia and requirement for insulin treatment (Stage 3). Several immune interventions have been shown to delay decline in beta cell function when studied in recent-onset clinical T1D[6]. One promising therapy is the FcR non-binding anti-CD3 monoclonal antibody teplizumab, as several studies have shown that short-term treatment reduces loss of β cell function durably, with an observable effect seen as long as 7 years after diagnosis and treatment[7-11]. The drug modifies the function of CD8+T lymphocytes, which are thought to be important effector cells that cause beta cell killing[12,13].

To date, no intervention initiated before the clinical diagnosis (i.e., at Stage 1 or 2) has altered progression to clinical, Stage 3 T1D. Thus, a need exists for a treatment that would prevent or delay the onset of clinical T1D in high-risk individuals.

SUMMARY

In one aspect, a method of preventing or delaying the onset of clinical type 1 diabetes (T1D) is provided, comprising:
providing a non-diabetic subject who is at risk for T1D;
determining that the non-diabetic subject (1) is substantially free of antibodies against zinc transporter 8 (ZnT8), (2) is HLA-DR4+, and/or (3) is not HLA-DR3+; and
administering a prophylactically effective amount of an anti-CD3 antibody to the non-diabetic subject.

In some embodiments, the non-diabetic subject is a relative of a patient with T1D. In certain embodiments, the non-diabetic subject has 2 or more diabetes-related autoantibodies selected from islet cell antibodies (ICA), insulin autoantibodies (IAA), and antibodies to glutamic acid decarboxylase (GAD), tyrosine phosphatase (IA-2/ICA512) or ZnT8.

In some embodiments, the detection of T1D-associated autoantibodies is done by point-of-care (POC) screening methods in the general population, or relatives of patients with T1D. Those POC methods can be qualitative rapid lateral flow tests.

In some embodiments, the non-diabetic subject has an infection by coxsackie B virus (CVB) and/or other beta-cell tropic virus(es). In some embodiments, this subject infected with a beta cell-tropic virus has HLA-DR4 and is more responsive to teplizumab.

In various embodiments, the non-diabetic subject has abnormal glucose tolerance on oral glucose tolerance test (OGTT). Abnormal glucose tolerance on OGTT is defined as a fasting glucose level of 110-125 mg/dL, or 2 hour plasma of ≥140 and <200 mg/dL, or an intervening glucose value at 30, 60, or 90 minutes on OGTT >200 mg/dL.

In some embodiments, the non-diabetic subject does not have antibodies against ZnT8. In certain embodiments, the non-diabetic subject is HLA-DR4+ and is not HLA-DR3+.

In one embodiment, the anti-CD3 antibody is teplizumab.

In various embodiments, the prophylactically effective amount comprises a 10 to 14 day daily course of subcutaneous (SC) injection or intravenous (IV) infusion of the anti-CD3 antibody, e.g., teplizumab, at 10-1000 micrograms/meter squared ($\mu g/m^2$), for a total dose of 6-15 milligrams of anti-CD3/teplizumab, preferably a 14-day course IV infusion of teplizumab at 51 $\mu g/m^2$, 103 $\mu g/m^2$, 207 $\mu g/m^2$, and 413 $\mu g/m^2$, on days 0-3, respectively, and one dose of 826 $\mu g/m^2$ on each of days 4-13. In certain embodiments, the prophylactically effective amount of the anti-CD3 antibody, e.g., teplizumab, delays median time to clinical diagnosis of T1D by at least 50%, at least 80%, or at least 90%, or at least 12 months, at least 18 months, at least 24 months, at least 36 months, at least 48 months, or at least 60 months, or longer.

In some embodiments, the anti-CD3 antibody, e.g., teplizumab, otelixizumab or foralumab, is administered in a SC pump or embedded in a slow-release biomaterial or administered orally. In other embodiments, the anti-CD3 antibody, e.g., teplizumab, otelixizumab or foralumab, is embedded in a biomaterial encapsulating beta cell precursors or beta cells or provided parenterally in conjunction with beta cell precursors or beta cells.

In some embodiments, the anti-CD3 antibody, e.g., teplizumab, otelixizumab or foralumab, is administered in combination with other pharmacological agents, such as metabolic agents, B cell inhibitors or other immune modulating agents.

In some embodiments, the anti-CD3 antibody, e.g., teplizumab, otelixizumab or foralumab, is administered with antigen-specific immune therapies and/or vaccines.

In some embodiments, the method further comprises determining, by flow cytometry, a frequency of TIGIT+ KLRG1+CD8+ T-cells in peripheral blood mononuclear cells of the non-diabetic subject, wherein an increase in the frequency after administrating the anti-CD3 antibody, e.g., teplizumab, otelixizumab or foralumab, indicates responsiveness to the anti-CD3 antibody, e.g., teplizumab.

Another aspect relates to a method of prognosing responsiveness of an anti-CD3 antibody, e.g., teplizumab, otelixizumab or foralumab, in preventing or delaying the onset of type 1 diabetes (T1D), comprising:
providing a non-diabetic subject who is at risk for T1D;
administering a prophylactically effective amount of teplizumab, otelixizumab or foralumab to the non-diabetic subject; and
determining, by flow cytometry, a frequency of TIGIT+ KLRG1+CD8+ T-cells in peripheral blood mononuclear cells of the non-diabetic subject, wherein an increase in the frequency indicates responsiveness to the anti-CD3 antibody, e.g., teplizumab, otelixizumab or foralumab.

In some embodiments, the method can further include determining that the non-diabetic subject (1) is substantially free of antibodies against zinc transporter 8 (ZnT8), (2) is HLA-DR4+, and/or (3) is not HLA-DR3+.

It will be clear for the person skilled in the art that aspects and/or embodiments as described herein may be combined.

BRIEF DESCRIPTION OF THE DRAWINGS

FIGS. 2A-2C: Effects of teplizumab treatment on development of T1D. FIG. 2A. Kaplan-Meier estimates of the proportion of participants who were diabetes free. The overall hazard ratio was 0.437 (95% CI:0.229, 0.832) (p=0.006, one sided, Cox model). The median time to T1D was 48.4 mos for teplizumab group and 24.4 mos for the placebo group. The insert shows the total number of subjects with T1D and diabetes free at the conclusion of the study. FIG. 2B. Frequency of type I diabetes by treatment group and cumulative and interval hazard ratios (95% confidence Intervals) by year on-study. (* The number of participants developing T1D in each treatment arm during the year interval are shown. In addition, the cumulative HRs and the HR for each year interval were calculated. † Mantel-Haenszel method applied to time-to-event data, both chi-square test and hazard ratio estimate[34]. € Likelihood ratio test and hazard ratio estimate and 95% CI from the Cox model). FIG. 2C. Absolute lymphocyte counts (ALC) in the study groups.

FIGS. 3A-3E: Immunologic effects and subgroup analysis of responses to teplizumab. FIG. 3A. Frequency of CD8+ KLRG1+TIGIT+CD57− T-cells in the teplizumab and placebo treated subjects. (* p<0.05 in teplizumab- vs placebo-treated participants). The mean±95% CI are shown. The comparisons were made with an ANCOVA for each time point and corrected for the baseline values. In addition, there was a significant increase in the frequency of these cells in the teplizumab treated participants at 3 mos (p=0.009) and 6 mos (p=0.007) but not in the placebo treated participants (paired t-test). FIG. 3B. The ladder plot shows the hazard rate for each of the indicated features of the participants at baseline. The absence of anti-ZnT8 antibody (p=0.004, HR: 0.031 for negative, 0.657 for positive), presence of HLA-DR4 (p=0.004, HR: 1.47 for negative, 0.201 for positive), and absence of HLA-DR3 (p=0.01, HR:0.181 for negative, 0.907 for positive) had significant effects on the hazard ratio. The development of diabetes in patients with or without anti-ZnT8 antibodies at baseline (FIG. 3C), or positive or negative for HLA-DR3 (FIG. 3D) or HLA-DR4 (FIG. 3E) are shown.

FIG. 4: Monoclonal antibodies used in flow cytometry.

FIG. 6: FACS contour plots showing staining of TIGIT (Y axis) vs KLRG1 (X axis). Electronic gates were placed on live CD8+CD57− T cells and the expression of KLRG1 and TIGIT are shown in peripheral blood cells from 3 subjects treated with teplizumab (top row) and 3 subjects treated with placebo. The numbers refer to the proportion of the total gated cells in each quadrant. The quadrants were placed based on staining controls.

DETAILED DESCRIPTION

Figure 1:
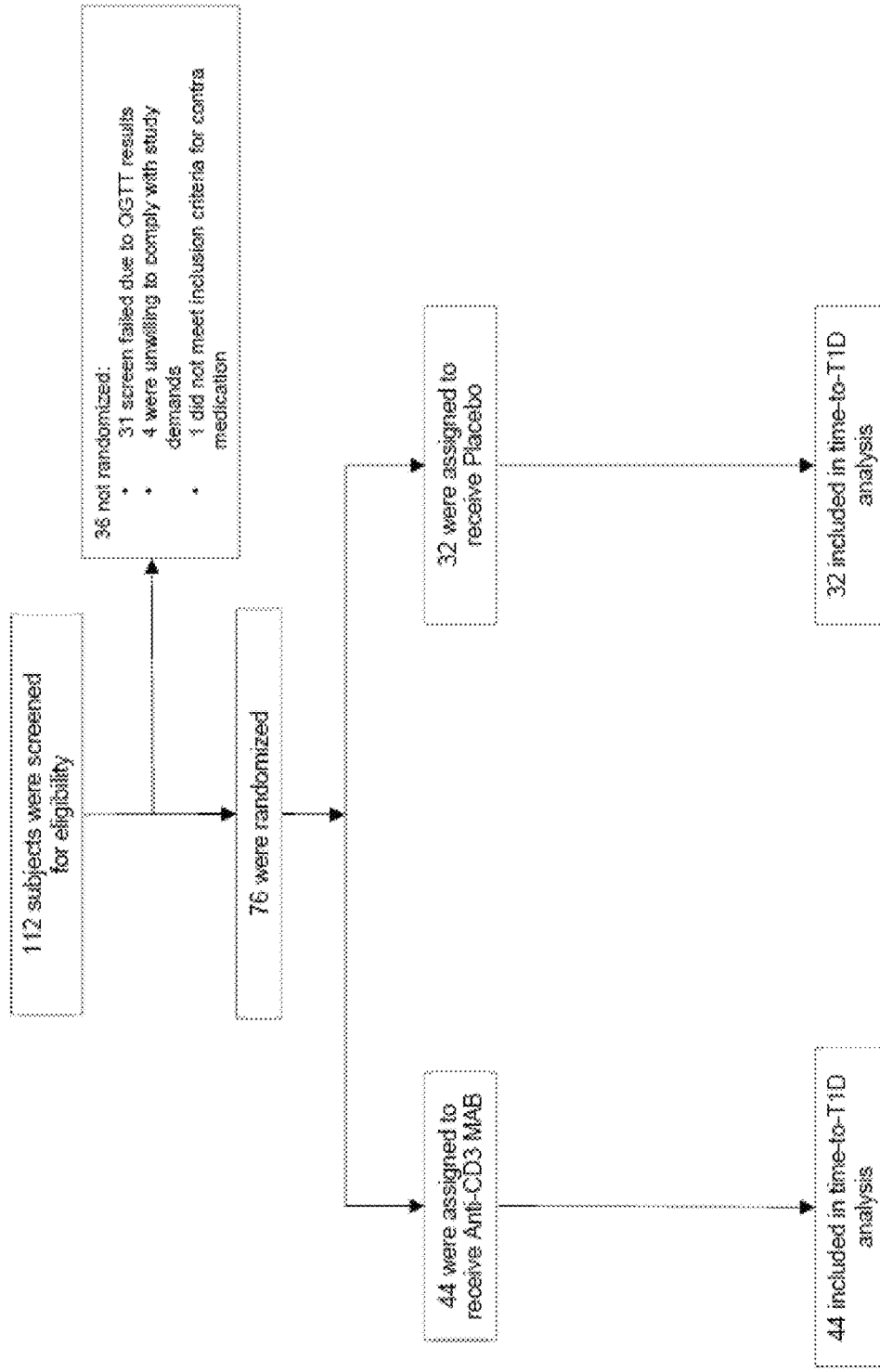
FIG. 1: Screening, enrollment and follow-up of the participants. A total of 112 subjects were screened for eligibility at TrialNet sites (see Appendix for a listing of study sites). Seventy-six of the subjects were randomized to the drug or placebo arms. They were infused with study drug at one of 14 TrialNet sites and followed, as per study protocol at one of 33 sites. All randomized subjects are included in the analysis.

The present disclosure provides, in some embodiments, the surprising discoveries that non-diabetic subjects who will respond to anti-CD3 antibody, e.g., teplizumab, treatment does not have antibodies against ZnT8. In certain embodiments, such non-diabetic subjects are HLA-DR4+ and are not HLA-DR3+. Unexpectedly, such non-diabetic subjects who will respond to the anti-CD3 antibody treatment demonstrate an increase, following teplizumab administration (e.g., after 1 month, after 2 months, after 3 months, or longer or shorter), in the frequency (or relative amount) of TIGIT+KLRG1+CD8+ T-cells (e.g., by flow cytometry) in peripheral blood mononuclear cells.

Provided herein, in some embodiments, is a method of preventing or delaying the onset of clinical type 1 diabetes (T1D), comprising: providing a non-diabetic subject who is at risk for T1D; determining that the non-diabetic subject (1) is substantially free of antibodies against zinc transporter 8 (ZnT8), (2) is HLA-DR4+, and/or (3) is not HLA-DR3+;

and administering a prophylactically effective amount of an anti-CD3 antibody, e.g., teplizumab, to the non-diabetic subject.

In certain embodiments, a method of prognosing responsiveness of an anti-CD3 antibody, e.g., teplizumab, in preventing or delaying the onset of T1D is provided. The method can include: providing a non-diabetic subject who is at risk for T1D; administering a prophylactically effective amount of the anti-CD3 antibody, e.g., teplizumab, to the non-diabetic subject; and determining, by flow cytometry, a frequency of TIGIT+KLRG1+CD8+ T-cells in peripheral blood mononuclear cells of the non-diabetic subject, wherein an increase in the frequency indicates responsiveness to the anti-CD3 antibody, e.g., teplizumab.

Definitions

Certain terms are defined herein below. Additional definitions are provided throughout the application.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values. The term "substantially" means more than 50%, preferably more than 80%, and most preferably more than 90% or 95%.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

As used herein, the term "prophylactic agent" refer to CD3 binding molecules such as teplizumab which can be used in the prevention, treatment, management or amelioration of one or more symptoms of T1D.

As used herein, the term "onset" of disease with reference to Type-1 diabetes refers to a patient meeting the criteria established for diagnosis of Type-1 diabetes by the American Diabetes Association (see, Mayfield et al., 2006, Am. Fam. Physician 58:1355-1362).

As used herein, the terms "prevent", "preventing" and "prevention" refer to the prevention of the onset of one or more symptoms of T1D in a subject resulting from the administration of a prophylactic or therapeutic agent.

As used herein, a "protocol" includes dosing schedules and dosing regimens. The protocols herein are methods of use and include prophylactic and therapeutic protocols. A "dosing regimen" or "course of treatment" may include administration of several doses of a therapeutic or prophylactic agent over 1 to 20 days.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey or a human), and more preferably a human.

As used herein, the term "prophylactically effective amount" refers to that amount of teplizumab sufficient to result in the delay or prevention of the development, recurrence or onset of one or more symptoms of T1D. In some embodiments, a prophylactically effective amount preferably refers to the amount of teplizumab that delays a subject's onset of T1D by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%.

Various aspects of the disclosure are described in further detail below. Additional definitions are set out throughout the specification.

Anti-CD3 Antibodies and Pharmaceutical Compositions

The terms "anti-CD3 antibody" and "an antibody that binds to CD3" refer to an antibody or antibody fragment that is capable of binding cluster of differentiation 3 (CD3) with sufficient affinity such that the antibody is useful as a prophylactic, diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (MA). In certain embodiments, an antibody that binds to CD3 has a dissociation constant (Kd) of <1 µM, <100 nM, <10 nM, <1 nM, <0.1 nM, <0.01 nM, or <0.001 nM (e.g. $10^{-8}$M or less, e.g. from $10^{-8}$M to $10^{-13}$M, e.g., from $10^{-9}$ M to $10^{-13}$M). In certain embodiments, an anti-CD3 antibody binds to an epitope of CD3 that is conserved among CD3 from different species.

In one embodiment, the anti-CD3 antibody can be ChAglyCD3 (otelixizumab). Otelixizumab is a humanized Fc nonbinding anti-CD3, which was evaluated initially in phase 2 studies by the Belgian Diabetes Registry (BDR) and then developed by Tolerx, which then partnered with GSK to conduct the phase 3 DEFEND new onset T1D trials (NCT00678886, NCT01123083, NCT00763451). Otelixizumab is administered IV with infusions over 8 days. See, e.g., Wiczling et al., J. Clin. Pharmacol. 50 (5) (May 2010) 494-506; Keymeulen et al., N Engl J Med. 2005; 352:2598-608; Keymeulen et al., Diabetologia. 2010; 53:614-23; Hagopian et al., Diabetes. 2013; 62:3901-8; Aronson et al., Diabetes Care. 2014; 37:2746-54; Ambery et al., Diabet Med. 2014; 31:399-402; Bolt et al., Eur. J. Immunol. lYY3. 23: 403-411; Vlasakakis et al., Br J Clin Pharmacol (2019) 85 704-714; Guglielmi et al, Expert Opinion on Biological Therapy, 16:6, 841-846; Keymeulen et al., N Engl J Med 2005; 352:2598-608; Keymeulen et al., BLOOD 2010, VOL 115, No. 6; Sprangers et al., Immunotherapy (2011) 3(11), 1303-1316; Daifotis et al., Clinical Immunology (2013) 149, 268-278; all incorporated herein by reference.

In another embodiment, the anti-CD3 antibody can be visilizumab (also called HuM291; Nuvion). Visilizumab is a humanized anti-CD3 monoclonal antibody characterized by a mutated IgG2 isotype, lack of binding to Fcγ receptors, and the ability to induce apoptosis selectively in activated T cells. It has evaluated in patients in graft-versus-host disease (NCT00720629; NCT00032279) and in ulcerative colitis (NCT00267306) and Crohn's Disease (NCT00267709). See, e.g., Sandborn et al., Gut 59 (11) (November 2010) 1485-1492, incorporated herein by reference.

In another embodiment, the anti-CD3 antibody can be foralumab, a fully human anti-CD3 monoclonal antibody being developed by Tiziana Life Sciences, PLC in NASH and T2D (NCT03291249). See, e.g., Ogura et al., Clin Immunol. 2017; 183:240-246; Ishikawa et al., Diabetes. 2007; 56(8):2103-9; Wu et al., J Immunol. 2010; 185(6): 3401-7; all incorporated herein by reference.

In another embodiment, the anti-CD3 antibody can be teplizumab. Teplizumab, also known as hOKT3yl (Ala-Ala) (containing an alanine at positions 234 and 235) is an anti-CD3 antibody that had been engineered to alter the function of the T lymphocytes that mediate the destruction of the insulin-producing beta cells of the islets of the pancreas. Teplizumab binds to an epitope of the CD3s chain expressed on mature T cells and by doing so changes their function. Sequences and compositions of teplizumab are disclosed in U.S. Pat. Nos. 6,491,916; 8,663,634; and 9,056, 906, each incorporated herein by reference in its entirety. The full sequences of light and heavy chains are set forth below. Bolded portions are the complementarity determining regions.

```
Teplizumab Light Chain (SEQ ID NO: 1):
DIQMTQSPSSLSASVGDRVTITCSASSSVSYMNWYQQTPGKAPKRWIYDT

SKLASGVPSRFSGSGSGTDYTFTISSLQPEDIATYYCQQWSSNPFTFGQG

TKLQITRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

Teplizumab Heavy Chain (SEQ ID NO: 2):
QVQLVQSGGGVVQPGRSLRLSCKASGYTFTRYTMHWVRQAPGKGLEWIGY

INPSRGYTNYNQKVKDRFTISRDNSKNTAFLQMDSLRPEDTGVYFCARYY

DDHYCLDYWGQGTPVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLEPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

In some embodiments, provided herein is a pharmaceutical composition. Such compositions comprise a prophylactically effective amount of an anti-CD3 antibody, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like (See, for example, Handbook of Pharmaceutical Excipients, Arthur H. Kibbe (ed., 2000, which is incorporated by reference herein in its entirety), Am. Pharmaceutical Association, Washington, D.C.

The composition, if desired, can also contain minor amounts of wetting or emulsifying agents, or pH buffering agents. These compositions can take the form of solutions, suspensions, emulsion, tablets, pills, capsules, powders, sustained release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a prophylactically or therapeutically effective amount of a prophylactic or therapeutic agent preferably in purified form, together with a suitable amount of carrier so as to provide the form for proper administration to the patient. The formulation should suit the mode of administration. In a preferred embodiment, the pharmaceutical compositions are sterile and in suitable form for administration to a subject, preferably an animal subject, more preferably a mammalian subject, and most preferably a human subject.

In a specific embodiment, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering the anti-CD3 antibody, care must be taken to use materials to which the anti-CD3 antibody does not absorb.

In another embodiment, the composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the composition can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the antibodies of the invention or fragments thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the lungs, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more antibodies of the invention or fragments thereof. See, e.g., U.S. Pat. No. 4,526,938; PCT publication WO 91/05548; PCT publication WO 96/20698; Ning et al., 1996, Radiotherapy & Oncology 39:179-189; Song et al., 1995, PDA Journal of Pharmaceutical Science & Technology 50:372-397; Cleek et al., 1997, Pro. Int'l. Symp. Control. Rel. Bioact. Mater. 24:853-854; and Lam et al., 1997, Proc. Int'l. Symp. Control Rel. Bioact. Mater. 24:759-760, each of which is incorporated herein by reference in its entirety.

A pharmaceutical composition can be formulated to be compatible with its intended route of administration. Examples of routes of administration include, but are not limited to, parenteral, e.g., intravenous, intradermal, subcutaneous, oral, intranasal (e.g., inhalation), transdermal (topical), transmucosal, and rectal administration. In a specific embodiment, the composition is formulated in accordance with routine procedures as a pharmaceutical composition adapted for intravenous, subcutaneous, intramuscular, oral, intranasal or topical administration to human beings. In a preferred embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

The compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In specific embodiments, the disclosure provides dosage forms that permit administration of the anti-CD3 antibody continuously over a period of hours or days (e.g., associated with a pump or other device for such delivery), for example, over a period of 1 hour, 2 hours, 3 hours, 4 hours, 6 hours, 8 hours, 10 hours, 12 hours. 16 hours, 20 hours, 24 hours, 30 hours, 36 hours, 4 days, 5 days, 7 days, 10 days or 14 days. In other specific embodiments, the invention provides dosage forms that permit administration of a continuously increasing dose, for example, increasing from 51 ug/m$^2$/day to 826 ug/m$^2$/day over a period of 24 hours, 30 hours, 36 hours, 4 days, 5 days, 7 days, 10 days or 14 days.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of the compositions disclosed herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In particular, the disclosure provides that the anti-CD3 antibodies, or pharmaceutical compositions thereof, can be packaged in a hermetically sealed container such as an ampoule or sachette indicating the quantity of the agent. In one embodiment, the anti-CD3 antibody, or pharmaceutical compositions thereof is supplied as a dry sterilized lyophilized powder or water free concentrate in a hermetically sealed container and can be reconstituted, e.g., with water or saline to the appropriate concentration for administration to a subject. Preferably, the anti-CD3 antibody, or pharmaceutical compositions thereof is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic agents, or pharmaceutical compositions herein should be stored at between 2 and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, the pharmaceutical composition is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

In a particular embodiment, the disclosure provides that the composition of the invention is packaged in a hermetically sealed container such as an ampoule or sachette indicating the quantity of the anti-CD3 antibody.

The compositions may, if desired, be presented in a pack or dispenser device that may contain one or more unit dosage forms containing the active ingredient. The pack may for example comprise metal or plastic foil, such as a blister pack.

The amount of the composition of the invention which will be effective in the prevention or amelioration of one or more symptoms associated with T1D can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

Methods and Use

In certain embodiments, the present disclosure encompasses administration of anti-human CD3 antibodies such teplizumab to individuals predisposed to develop type 1 diabetes or with pre-clinical stages of type 1 diabetes, but who do not meet the diagnosis criteria as established by the American Diabetes Association or the Immunology of Diabetes Society to prevent or delay the onset of type 1 diabetes and/or to prevent or delay the need for administration of insulin to such patients. In certain embodiments, high-risk factors for identification of predisposed subjects include having first or second degree relatives with diagnosed type-1 diabetes, an impaired fasting glucose level (e.g., at least one determination of a glucose level of 100-125 mg/dl after fasting (8 hour with no food)), an impaired glucose tolerance in response to a 75 g OGTT (e.g., at least one determination of a 2-hr glucose level of 140-199 mg/dl in response to a 75 g OGTT), an HLA type of DR3, DR4 or DR7 in a Caucasian, an HLA type of DR3 or DR4 in a person of African descent, an HLA type of DR3, DR4 or DR9 in a person of Japanese descent, exposure to viruses (e.g., coxsackie B virus, enteroviruses, adenoviruses, rubella, cytomegalovirus, Epstein-Barr virus), a positive diagnosis according to art accepted criteria of at least one other autoimmune disorder (e.g., thyroid disease, celiac disease), and/or the detection of autoantibodies, particularly ICAs and type 1 diabetes-associated autoantibodies, in the serum or other tissues. In certain embodiments, the subject identified as predisposed to developing type 1 diabetes has at least one of the risk factors described herein and/or as known in the art. The present disclosure also encompasses identification of subjects predisposed to development of type 1 diabetes, wherein said subject presents a combination of two or more, three or more, four or more, or more than five of the risk factors disclosed herein or known in the art.

Serum autoantibodies associated with type 1 diabetes or with a predisposition for the development of type 1 diabetes are islet-cell autoantibodies (e.g., anti-ICA512 autoantibodies), glutamic acid decarbamylase autoantibodies (e.g., anti-GAD65 autoantibodies), IA2 antibodies, ZnT8 antibodies and/or anti-insulin autoantibodies. Accordingly, in a specific example in accordance with this embodiment, the invention encompasses the treatment of an individual with detectable autoantibodies associated with a predisposition to the development of type 1 diabetes or associated with early stage type 1 diabetes (e.g., anti-IA2, anti-ICA512, anti-GAD or anti-insulin autoantibodies), wherein said individual has not been diagnosed with type 1 diabetes and/or is a first or second degree relative of a type-1 diabetic. In certain embodiments, the presence of the autoantibodies is detected by ELISA, electrochemoluminescence (ECL), radioassay (see, e.g., Yu et al., 1996, J. Clin. Endocrinol. Metab. 81:4264-4267), agglutination PCR (Tsai et al, *ACS Central Science* 2016 2 (3), 139-147) or by any other method for immunospecific detection of antibodies described herein or as known to one of ordinary skill in the art.

β-cell function prior to, during, and after therapy may be assessed by methods described herein or by any method known to one of ordinary skill in the art. For example, the Diabetes Control and Complications Trial (DCCT) research group has established the monitoring of percentage glycosylated hemoglobin (HA1 and HA1c) as the standard for evaluation of blood glucose control (DCCT, 1993, N. Engl. J. Med. 329:977-986). Alternatively, characterization of daily insulin needs, C-peptide levels/response, hypoglycemic episodes, and/or FPIR may be used as markers of β-cell function or to establish a therapeutic index (See Keymeulen et al., 2005, N. Engl. J. Med. 352:2598-2608; Herold et al., 2005, Diabetes 54:1763-1769; U.S. Pat. Appl. Pub. No. 2004/0038867 A1; and Greenbaum et al., 2001, Diabetes 50:470-476, respectively). For example, FPIR is calculated as the sum of insulin values at 1 and 3 minutes post IGTT, which are performed according to Islet Cell Antibody Register User's Study protocols (see, e.g., Bingley et al., 1996, Diabetes 45:1720-1728 and McCulloch et al., 1993, Diabetes Care 16:911-915).

In some embodiments, the individuals predisposed to develop T1D can be a non-diabetic subject who is a relative of a patient with T1D. In certain embodiments, the non-diabetic subject has 2 or more diabetes-related autoantibodies selected from islet cell antibodies (ICA), insulin autoantibodies (IAA), and antibodies to glutamic acid decarboxylase (GAD), tyrosine phosphatase (IA-2/ICA512) or ZnT8.

In various embodiments, the non-diabetic subject has abnormal glucose tolerance on oral glucose tolerance test (OGTT). Aabnormal glucose tolerance on OGTT is defined as a fasting glucose level of 110-125 mg/dL, or 2 hour plasma of ≥140 and <200 mg/dL, or an intervening glucose value at 30, 60, or 90 minutes on OGTT >200 mg/dL.

In some embodiments, the non-diabetic subject who will respond to the anti-CD3 antibody such as teplizumab does not have antibodies against ZnT8. In certain embodiments, such non-diabetic subject is HLA-DR4+ and is not HLA-DR3+. In some embodiments, such non-diabetic subject who will respond to the anti-CD3 antibody such as teplizumab demonstrates an increase, following administration (e.g., after 1 month, after 2 months, after 3 months, or longer or shorter), in the frequency (or relative amount) of TIGIT+ KLRG1+CD8+ T-cells (e.g., by flow cytometry) in peripheral blood mononuclear cells.

In various embodiments, the prophylactically effective amount comprises a 10 to 14 day course of subcutaneous (SC) injection or intravenous (IV) infusion of the anti-CD3 antibody such as teplizumab at 10-1000 micrograms/meter squared ($\mu g/m^2$). In one example, the prophylactically effective amount comprises a 14-day course IV infusion of the anti-CD3 antibody such as teplizumab at 51 $\mu g/m^2$, 103 $\mu g/m^2$, 207 $\mu g/m^2$, and 413 $\mu g/m^2$, on days 0-3, respectively, and one dose of 826 $\mu g/m^2$ on each of days 4-13. In certain embodiments, the prophylactically effective amount delays median time to clinical diagnosis of T1D by at least 50%, at least 80%, or at least 90%, or at least 12 months, at least 18 months, at least 24 months, at least 36 months, at least 48 months, or at least 60 months, or longer.

In certain embodiments, the course of dosing with the anti-CD3 antibody such as teplizumab can be repeated at 2 month, 4 month, 6 month, 8 month, 9 month, 10 month, 12 month, 15 month, 18 month, 24 month, 30 month, or 36 month intervals. In specific embodiments efficacy of the treatment with the anti-CD3 antibody such as teplizumab is determined as described herein or as is known in the art at 2 months, 4 months, 6 months, 9 months, 12 months, 15 months, 18 months, 24 months, 30 months, or 36 months subsequent to the previous treatment.

In another embodiment, a subject is administered one or more unit doses of approximately 0.5-50 ug/kg, approximately 0.5-40 ug/kg, approximately 0.5-30 ug/kg, approximately 0.5-20 ug/kg, approximately 0.5-15 ug/kg, approximately 0.5-10 ug/kg, approximately 0.5-5 ug/kg, approximately 1-5 ug/kg, approximately 1-10 ug/kg, approximately 20-40 ug/kg, approximately 20-30 ug/kg, approximately 22-28 ug/kg or approximately 25-26 ug/kg of the anti-CD3 antibody such as teplizumab to prevent, treat or ameliorate one or more symptoms of T1D. In another embodiment, a subject is administered one or more unit doses of about 200 ug/kg, 178 ug/kg, 180 ug/kg, 128 ug/kg, 100 ug/kg, 95 ug/kg, 90 ug/kg, 85 ug/kg, 80 ug/kg, 75 ug/kg, 70 ug/kg, 65 ug/kg, 60 ug/kg, 55 ug/kg, 50 ug/kg, 45 ug/kg, 40 ug/kg, 35 ug/kg, 30 ug/kg, 26 ug/kg, 25 ug/kg, 20 ug/kg, 15 ug/kg, 13 ug/kg, 10 ug/kg, 6.5 ug/kg, 5 ug/kg, 3.2 ug/kg, 3 ug/kg, 2.5 ug/kg, 2 ug/kg, 1.6 ug/kg, 1.5 ug/kg, 1 ug/kg, 0.5 ug/kg, 0.25 ug/kg, 0.1 ug/kg, or 0.05 ug/kg of the anti-CD3 antibody such as teplizumab to prevent, treat or ameliorate one or more symptoms of T1D.

In particular embodiments, a subject is administered one or more doses of the anti-CD3 antibody such as teplizumab at about 5-1200 ug/m2, preferably, 51-826 ug/m2. In another embodiment, a subject is administered one or more unit doses of 1200 ug/m2, 1150 ug/m2, 1100 ug/m2, 1050 ug/m2, 1000 ug/m2, 950 ug/m2, 900 ug/m2, 850 ug/m2, 800 ug/m2, 750 ug/m2, 700 ug/m2, 650 ug/m2, 600 ug/m2, 550 ug/m2, 500 ug/m2, 450 ug/m2, 400 ug/m2, 350 ug/m2, 300 ug/m2, 250 ug/m2, 200 ug/m2, 150 ug/m2, 100 ug/m2, 50 ug/m2, 40 ug/m2, 30 ug/m2, 20 ug/m2, 15 ug/m2, 10 ug/m2, or 5 ug/m2 of the anti-CD3 antibody such as teplizumab to prevent, treat, slow the progression of, delay the onset of or ameliorate one or more symptoms of T1D.

In another embodiment, the subject is administered a treatment regimen comprising one or more doses of a prophylactically effective amount of the anti-CD3 antibody such as teplizumab, wherein the course of treatment is administered over 2 days, 3 days, 4 days, 5 days, 6 days, 7 days, 8 days, 9 days, 10 days, 11 days, 12 days, 13 days or 14 days. In one embodiment, the treatment regimen comprises administering doses of the prophylactically effective amount every day, every 2nd day, every 3rd day or every 4th day. In certain embodiments, the treatment regimen comprises administering doses of the prophylactically effective amount on Monday, Tuesday, Wednesday, Thursday of a given week and not administering doses of the prophylactically effective amount on Friday, Saturday, and Sunday of the same week until 14 doses, 13, doses, 13 doses, 12 doses, 11 doses, 10 doses, 9 doses, or 8 doses have been administered. In certain embodiments the dose administered is the same each day of the regimen.

In certain embodiments, a subject is administered a treatment regimen comprising one or more doses of a prophylactically effective amount of the anti-CD3 antibody such as teplizumab, wherein the prophylactically effective amount is 200 ug/kg/day, 175 ug/kg/day, 150 ug/kg/day, 125 ug/kg/day, 100 ug/kg/day, 95 ug/kg/day, 90 ug/kg/day, 85 ug/kg/day, 80 ug/kg/day, 75 ug/kg/day, 70 ug/kg/day, 65 ug/kg/day, 60 ug/kg/day, 55 ug/kg/day, 50 ug/kg/day, 45 ug/kg/day, 40 ug/kg/day, 35 ug/kg/day, 30 ug/kg/day, 26 ug/kg/day, 25 ug/kg/day, 20 ug/kg/day, 15 ug/kg/day, 13 ug/kg/day, 10 ug/kg/day, 6.5 ug/kg/day, 5 ug/kg/day, 3.2 ug/kg/day, 3 ug/kg/day, 2.5 ug/kg/day, 2 ug/kg/day, 1.6 ug/kg/day, 1.5 ug/kg/day, 1 ug/kg/day, 0.5 ug/kg/day, 0.25 ug/kg/day, 0.1 ug/kg/day, or 0.05 ug/kg/day; and/or wherein the prophylactically effective amount is 1200 ug/m2/day, 1150 ug/m2/day, 1100 ug/m2/day, 1050 ug/m2/day, 1000 ug/m2/day, 950 ug/m2/day, 900 ug/m2/day, 850 ug/m2/day, 800 ug/m2/day, 750 ug/m2/day, 700 ug/m2/day, 650 ug/m2/day, 600 ug/m2/day, 550 ug/m2/day, 500 ug/m2/day, 450 ug/m2/day, 400 ug/m2/day, 350 ug/m2/day, 300 ug/m2/day, 250 ug/m2 day, 200 ug/m2/day, 150 ug/m2/day, 100 ug/m2/day, 50 ug/m2/day, 40 ug/m2 day, 30 ug/m2/day, 20 ug/m2/day, 15 ug/m2/day, 10 ug/m2/day, or 5 ug/m2/day.

In another embodiment, the intravenous dose of 1200 ug/m2 or less, 1150 ug/m2 or less, 1100 ug/m2 or less, 1050 ug/m2 or less, 1000 ug/m2 or less, 950 ug/m2 or less, 900 ug/m2 or less, 850 ug/m2 or less, 800 ug/m2 or less, 750 ug/m2 or less, 700 ug/m2 or less, 650 ug/m2 or less, 600 ug/m2 or less, 550 ug/m2 or less, 500 ug/m2 or less, 450 ug/m2 or less, 400 ug/m2 or less, 350 ug/m2 or less, 300 ug/m2 or less, 250 ug/m2 or less, 200 ug/m2 or less, 150 ug/m2 or less, 100 ug/m2 or less, 50 ug/m2 or less, 40 ug/m2 or less, 30 ug/m2 or less, 20 ug/m2 or less, 15 ug/m2 or less, 10 ug/m2 or less, or 5 ug/m2 or less of the anti-CD3 antibody such as teplizumab is administered over about 24 hours, about 22 hours, about 20 hours, about 18 hours, about 16 hours, about 14 hours, about 12 hours, about 10 hours, about 8 hours, about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to prevent, treat or ameliorate one or more symptoms of type 1 diabetes. The total dosage over the duration of the regimen is preferably a total of less than 9000 ug/m2, 8000 ug/m2, 7000 ug/m2, 6000 ug/m2, and may be less than 5000 ug/m2, 4000 ug/m2, 3000 ug/m2, 2000 ug/m2, or 1000 ug/m2. In specific embodiments, the total dosage administered in the regimen is 100 ug/m2 to 200 ug/m2, 100 ug/m2 to 500 ug/m2, 100 ug/m2 to 1000 ug/m2, or 500 ug/m2 to 1000 ug/m2.

In preferred embodiments, the dose escalates over the first fourth, first half or first ⅔ of the doses (e.g., over the first 2, 3, 4, 5, or 6 days of a 10, 12, 14, 16, 18 or 20 day regimen of one dose per day) of the treatment regimen until the daily prophylactically effective amount of the anti-CD3 antibody such as teplizumab is achieved. In certain embodiments, a subject is administered a treatment regimen comprising one or more doses of a prophylactically effective amount of the anti-CD3 antibody such as teplizumab, wherein the prophylactically effective amount is increased by, e.g., 0.01 ug/kg, 0.02 ug/kg, 0.04 ug/kg, 0.05 ug/kg, 0.06 ug/kg, 0.08 ug/kg, 0.1 ug/kg, 0.2 ug/kg, 0.25 ug/kg, 0.5 ug/kg, 0.75 ug/kg, 1 ug/kg, 1.5 ug/kg, 2 ug/kg, 4 ug/kg, 5 ug/kg, 10 ug/kg, 15 ug/kg, 20 .XI.g/kg, 25 ug/kg, 30 ug/kg, 35 ug/kg, 40 ug/kg, 45 ug/kg, 50 ug/kg, 55 ug/kg, 60 ug/kg, 65 ug/kg, 70 ug/kg, 75 ug/kg, 80 ug/kg, 85 ug/kg, 90 ug/kg, 95 ug/kg, 100 ug/kg, or 125 ug/kg each day; or increased by, e.g., 1 ug/m2, 5 ug/m2, 10 ug/m2, 15 ug/m2, 20 ug/m2, 30 ug/m2, 40 ug/m2, 50 ug/m2, 60 ug/m2, 70 ug/m2, 80 ug/m2, 90 ug/m2, 100 ug/m2, 150 ug/m2, 200 ug/m2, 250 ug/m2, 300 ug/m2, 350 ug/m2, 400 ug/m2, 450 ug/m2, 500 ug/m2, 550 ug/m2, 600 ug/m2, or 650 ug/m2, each day as treatment progresses. In certain embodiments, a subject is administered a treatment regimen comprising one or more doses of a prophylactically effective amount of the anti-CD3 antibody such as teplizumab, wherein the prophylactically effective amount is increased by a factor of 1.25, a factor of 1.5, a factor of 2, a factor of 2.25, a factor of 2.5, or a factor of 5 until the daily prophylactically effective amount of the anti-CD3 antibody such as teplizumab is achieved.

In a specific embodiment, a subject is intramuscularly administered one or more doses of a 200 ug/kg or less, preferably 175 ug/kg or less, 150 ug/kg or less, 125 ug/kg or less, 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.5 ug/kg or less of the anti-CD3 antibody such as teplizumab, otelixizumab or foralumab, to prevent, treat or ameliorate one or more symptoms of T1D.

In another embodiment, a subject is subcutaneously administered one or more doses of a 200 ug/kg or less, preferably 175 ug/kg or less, 150 ug/kg or less, 125 ug/kg or less, 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.5 ug/kg or less of the anti-CD3 antibody such as teplizumab, otelixizumab or foralumab, to prevent, treat or ameliorate one or more symptoms of T1D.

In another embodiment, a subject is intravenously administered one or more doses of a 100 ug/kg or less, preferably 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.5 ug/kg or less of the anti-CD3 antibody such as teplizumab, otelixizumab or foralumab, to prevent, treat or ameliorate one or more symptoms of T1D. In another embodiment, the intravenous dose of 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.5 ug/kg or less of the anti-CD3 antibody such as teplizumab, otelixizumab or foralumab, is administered over about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to prevent, treat or ameliorate one or more symptoms of T1D.

In another embodiment, a subject is orally administered one or more doses of a 100 ug/kg or less, preferably 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.5 ug/kg or less of the anti-CD3 antibody such as teplizumab, otelixizumab or foralumab, to prevent, treat or ameliorate one or more symptoms of T1D. In another embodiment, the oral dose of 100 ug/kg or less, 95 ug/kg or less, 90 ug/kg or less, 85 ug/kg or less, 80 ug/kg or less, 75 ug/kg or less, 70 ug/kg or less, 65 ug/kg or less, 60 ug/kg or less, 55 ug/kg or less, 50 ug/kg or less, 45 ug/kg or less, 40 ug/kg or less, 35 ug/kg or less, 30 ug/kg or less, 25 ug/kg or less, 20 ug/kg or less, 15 ug/kg or less, 10 ug/kg or less, 5 ug/kg or less, 2.5 ug/kg or less, 2 ug/kg or less, 1.5 ug/kg or less, 1 ug/kg or less, 0.5 ug/kg or less, or 0.5 ug/kg or less of the anti-CD3 antibody such as teplizumab, otelixizumab or foralumab, is administered over about 6 hours, about 4 hours, about 2 hours, about 1.5 hours, about 1 hour, about 50 minutes, about 40 minutes, about 30 minutes, about 20 minutes, about 10 minutes, about 5 minutes, about 2 minutes, about 1 minute, about 30 seconds or about 10 seconds to prevent, treat or ameliorate one or more symptoms of T1D.

In specific embodiments in which escalating doses are administered for the first days of the dosing regimen, the dose on day 1 of the regimen is 5-100 ug/m2/day, preferably 51 ug/m2/day and escalates to the daily dose as recited immediately above by day 3, 4, 5, 6 or 7. For example, on day 1, the subject is administered a dose of approximately 51 ug/m$^2$/day, on day 2 approximately 103 ug/m$^2$/day, on day 3 approximately 207 ug/m$^2$/day, on day 4 approximately 413 ug/m$^2$/day and on subsequent days of the regimen (e.g., days 5-14) 826 ug/m$^2$/day. In another embodiment, on day 1, the subject is administered a dose of approximately 227 ug/m$^2$/day, on day 2 approximately 459 ug/m$^2$/day, on day 3 and subsequent days, approximately 919 ug/m$^2$/day. In another embodiment, on day 1, the subject is administered a dose of approximately 284 ug/m$^2$/day, on day 2 approximately 574 ug/m$^2$/day, on day 3 and subsequent days, approximately 1148 ug/m$^2$/day.

In other embodiments, the initial dose is ¼, to ½, to equal to the daily dose at the end of the regimen but is administered in portions at intervals of 6, 8, 10 on 12 hours. For example, a 13 ug/kg/day dose is administered in four doses of 3-4 ug/kg at intervals of 6 hours to reduce the level of cytokine release caused by administration of the antibody. In specific embodiments, to reduce the possibility of cytokine release and other adverse effects, the first 1, 2, 3, or 4 doses or all the doses in the regimen are administered more slowly by intravenous administration. For example, a dose of 51 ug/m$^2$/day may be administered over about 5 minutes, about 15 minutes, about 30 minutes, about 45 minutes, about 1 hour, about 2 hours, about 4 hours, about 6 hours, about 8 hours, about 10 hours, about 12 hours, about 14 hours, about 16 hours, about 18 hours, about 20 hours, and about 22 hours. In certain embodiments, the dose is administered by slow infusion over a period of, e.g., 20 to 24 hours. In specific embodiments, the dose is infused in a pump, preferably increasing the concentration of antibody administered as the infusion progresses.

In other embodiments, a set fraction of the doses for the 51 ug/m$^2$/day to 826 ug/m$^2$/day regimen described above is administered in escalating doses. In certain embodiments, the fraction is ⅒, ¼, ⅓, ½, ⅔ or ¾ of the daily doses of the regimens described above. Accordingly, when the fraction is ⅒, the daily doses will be 5.1 ug/m$^2$ on day 1, 10.3 ug/m$^2$ on day 2, 20.7 g/m$^2$ on day 3, 41.3 ug/m$^2$ on day 4 and 82.6 ug/m$^2$ on days 5 to 14. When the fraction is ¼, the doses will be 12.75 ug/m$^2$ on day 1, 25.5 ug/m$^2$ on day 2, 51 ug/m$^2$ on day 3, 103 ug/m$^2$ on day 4, and 207 ug/m$^2$ on days 5 to 14. When the fraction is ⅓, the doses will be 17 ug/m$^2$ on day 1, 34.3 ug/m$^2$ on day 2, 69 ug/m$^2$ on day 3, 137.6 ug/m$^2$ on day 4, and 275.3 ug/m$^2$ on days 5 to 14. When the fraction is ½, the doses will be 25.5 ug/m² on day 1, 51 ug/m² on day 2, 103 ug/m² on day 3, 207 ug/m² on day 4, and 413 ug/m² on days 5 to 14. When the fraction is ⅔, the doses will be 34 ug/m² on day 1, 69 ug/m² on day 2, 137.6 ug/m² on day 3, 275.3 ug/m² on day 4, and 550.1 ug/m² on days 5 to 14. When the fraction is ¾, the doses will be 38.3 ug/m² on day 1, 77.3 ug/m² on day 2, 155.3 ug/m² on day 3, 309.8 ug/m² on day 4, and 620 ug/m² on days 5 to 14. In other embodiments, the regimen is identical to one of those described above but only over days 1 to 4, days 1 to 5, or days 1 to 6. For example, in a particular embodiment, the doses will be 17 ug/m² on day 1, 34.3 ug/m² on day 2, 69 ug/m² on day 3, 137.6 ug/m² on day 4, and 275.3 ug/m² on days 5 and 6.

In specific embodiments, the anti-CD3 antibody such as teplizumab, otelixizumab or foralumab, is not administered by daily doses over a number of days, but is rather administered by infusion in an uninterrupted manner over 4 hours, 6 hours, 8 hours, 10 hours, 12 hours, 15 hours, 18 hours, 20 hours, 24 hours, 30 hours or 36 hours. The infusion may be constant or may start out at a lower dosage for, for example, the first 1, 2, 3, 5, 6, or 8 hours of the infusion and then increase to a higher dosage thereafter. Over the course of the infusion, the patient receives a dose equal to the amount administered in the 5 to 20 day regimens set forth above. For example, a dose of approximately 150 ug/m², 200 ug/m², 250 ug/m², 500 ug/m², 750 ug/m², 1000 ug/m², 1500 ug/m², 2000 ug/m², 3000 ug/m², 4000 ug/m², 5000 ug/m², 6000 ug/m², 7000 ug/m², 8000 ug/m², or 9000 ug/m². In particular, the speed and duration of the infusion is designed to minimize the level of free anti-CD3 antibody such as teplizumab, otelixizumab or foralumab in the subject after administration. In certain embodiments, the level of free anti-CD3 antibody such as teplizumab should not exceed 200 ng/ml free antibody. In addition, the infusion is designed to achieve a combined T cell receptor coating and modulation of at least 50%, 60%, 70%, 80%, 90%, 95% or of 100%.

In other embodiments, the anti-CD3 antibody such as teplizumab, otelixizumab or foralumab is administered chronically to treat, prevent, or slow or delay the onset or progression, or ameliorate one or more symptoms of type 1 diabetes. For example, in certain embodiments, a low dose of the anti-CD3 antibody such as teplizumab is administered once a month, twice a month, three times per month, once a week or even more frequently either as an alternative to the 6 to 14 day dosage regimen discussed above or after administration of such a regimen to enhance or maintain its effect. Such a low dose may be anywhere from 1 ug/m² to 100 ug/m², such as approximately 5 ug/m², 10 ug/m², 15 ug/m², 20 ug/m², 25 ug/m², 30 ug/m², 35 ug/m², 40 ug/m², 45 ug/m², or 50 ug/m².

In other embodiments, the subject may be re-dosed at some time subsequent to administration of the the anti-CD3 antibody such as teplizumab, otelixizumab or foralumab dosing regimen, for example, based upon one or more physiological parameters or may be done as a matter of course. Such redosing may be administered and/or the need for such redosing evaluated 2 months, 4 months, 6 months, 8 months, 9 months, 1 year, 15 months, 18 months, 2 years, 30 months or 3 years after administration of a dosing regimen and may include administering a course of treatment every 6 months, 9 months, 1 year, 15 months, 18 months, 2 years, 30 months or 3 years indefinitely.

EXAMPLE

Abstract

Background: Type 1 diabetes (T1D) is a chronic autoimmune disease that leads to destruction of insulin producing beta cells and dependence on exogenous insulin for survival. Some interventions have shown success in attenuating the loss of insulin production in patients who present with clinical disease but no intervention to date has been able to affect progression to the disease in individuals who are at high risk for its development.

Methods: We conducted a randomized placebo controlled double blind study of teplizumab (FcR non-binding anti-CD3 mAb) in non-diabetic relatives of patients with T1D who were at high risk for the clinical disease. The patients were randomized to a single 14 day course of the drug or placebo and followed for the disease progression using oral glucose tolerance tests at approximately 6 month intervals.

Results: A total of 76 subjects were randomized, 44 in the teplizumab and 32 in the placebo arms. Seventy-two percent of the participants were children. Teplizumab treatment delayed the median time to clinical diagnosis of T1D from 24.4 to 48.4 months (Cox proportional hazards, p=0.006) and the rate of diabetes development from 9.8% to 4.1% per year. Drug treatment increased the proportion of TIGIT+ KLRG1+CD8+ T-cells. Participants who did not have antibodies against ZnT8 (p=0.01), who were HLA-DR4+ (p=0.006), and not HLA-DR3+(p=0.05) were most likely to respond to teplizumab.

Conclusions: Teplizumab can delay the diagnosis of T1D in high-risk individuals. Subgroups of individuals may be more likely to respond to therapy and the effects.

Methods

Trial Participants

Participants were identified through the TrialNet Natural History Study[14]. The trial was conducted between July 2011 and November 2018 at sites in the United States, Canada and Germany. Institutional Review Board (IRB) approval was obtained at each participating site. The patients, their parents, or both provided written informed consent prior to trial entry.

Eligible participants were nondiabetic relatives of patients with type 1 diabetes, age ≥8 years at time of randomization, who were at high risk for development of clinical diabetes. They had 2 or more diabetes-related autoantibodies on 2 sample collections within 6 months prior to randomization. In addition, they had abnormal glucose tolerance on oral glucose tolerance test (OGTT), defined to be a fasting glucose level of 110-125 mg/dL, or 2 hour plasma of >140 and <200 mg/dL, or an intervening glucose value at 30, 60, or 90 minutes on OGTT >200 mg/d on two occasions within 52 days of enrollment. The protocol was amended in 2014 to allow enrollment of participants <age 18 with a single abnormal OGTT because the rates of T1D progression were similar with and without a confirmatory OGTT in this age group. In these 8 subjects (5 in teplizumab and 3 in placebo arms) the second pre-treatment OGTT was done on the first day of study drug administration. Individuals with other significant medical history, abnormal laboratory chemistries or blood counts were excluded.

Patient Identification

Figure 5:
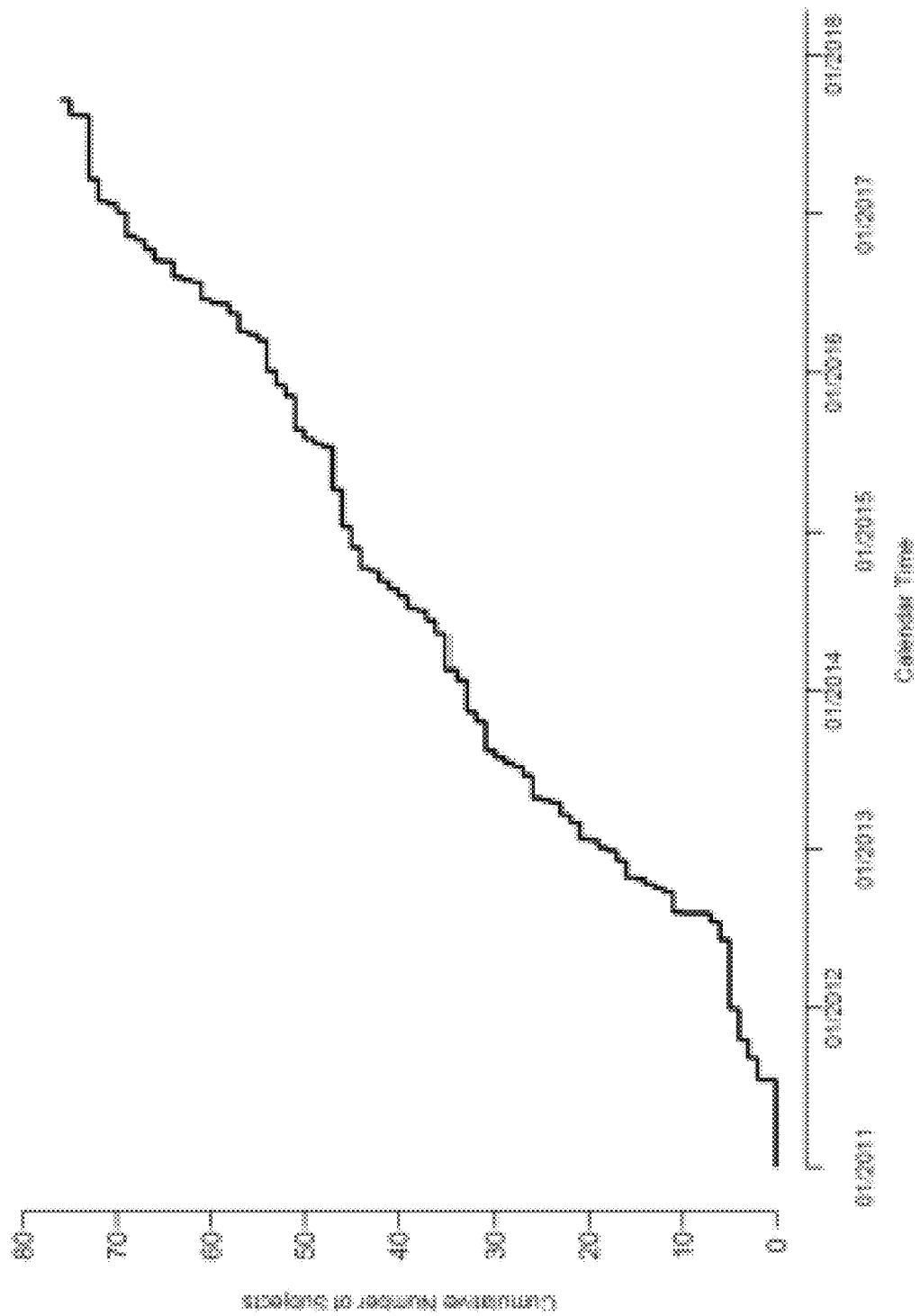
FIG. 5: Enrollment in trial.

Subjects were identified in the TrialNet Pathway to Prevention (PTP) study. See FIG. 5. The PTP study enrolled first degree relatives of patients with T1D, ages 1-45, and up to age 20 in second- or third-degree relatives, evaluated diabetes autoantibodies to microinsulin (mIAA), glutamic acid decarboxylase-65 (GAD), and insulinoma-associated antigen-2 (IA-2, or ICA512). Islet cell (ICA) and zinc transporter 8 (ZnT8) autoantibodies were measured if at least 1 other antibody tested positive.

Trial Design and Intervention

Participants were randomized to receive either teplizumab or placebo, in equal allocations to each group. Randomization was stratified at each TrialNet study site by age (< or >18 years), and glucose during the pre-randomization OGTT status. Treatment assignment was double masked.

Participants received a 14-day course of teplizumab or placebo administered as an outpatient in a clinical research center using the drug dosing regimen described previously[9,10]. Specifically, those assigned to active study drug received teplizumab by daily IV infusions of teplizumab according to the following daily schedule: 51 micrograms/meter squared ($\mu g/m^2$), 103 $\mu g/m^2$, 207 $\mu g/m^2$, and 413 $\mu g/m^2$ on Study Days 0-3, respectively, and one dose of 826 $\mu g/m^2$ on each of Study Days 4-13. Participants randomized to the placebo arm received a 14-day course of matching IV saline. Participants received ibuprofen and diphenhydramine prior to infusions on the first 5 days, and further dosing with ibuprofen, diphenhydramine and/or acetaminophen thereafter as needed for symptomatic relief. Protocol defined stopping criteria for study drug infusions were followed.

During the entire study, all subjects had interim contact with study personnel for formal inquiry about adverse events and symptoms of diabetes.

End Points and Assessments

The primary outcome was the elapsed time from randomization to the diagnosis of diabetes, using criteria defined by the American Diabetes Association[15].

Scheduled OGTT tests were done at 3 and 6 months after the infusion, and every 6 months thereafter. Screening random glucoses, were performed at 3 month intervals and OGTT tests were performed if the random glucose was >200 mg/dl with symptoms of diabetes. Diabetic OGTT tests needed to be sequentially confirmed and the date of diagnosis was identified as the time of the $2^{nd}$ diagnostic test. Outcome reviews were conducted without knowledge of treatment assignment.

Blood samples were analyzed centrally at TrialNet core laboratories with methods described in the Laboratory Methods. Flow cytometry was used to analyse CD8+ T-cell subsets in the peripheral blood (FIG. 4).

Laboratory Methods

C-peptide was measured from frozen plasma by two-site immunoenzymometric assay (Tosoh Bioscience, South San Francisco, Calif.). $HbA_{1c}$ was measured using ion-exchange high performance liquid chromatography (Variant II, Bio-Rad Diagnostics, Hercules, Calif.). Reliability coefficients for each assay were above 0.99 from split duplicate samples. mIAA, GAD-65Ab, ICA-512Ab, ZnT8A were measured using radio-immunobinding assays at the Barbara Davis Diabetes Center, Anschultz C O, and ICA using indirect immunofluorescence at the University of Florida at Gainesville. C-peptide, glucose and HbA1c were measured at the Northwest Research Laboratory, Seattle, Wash. C-peptide was measured from frozen plasma by two-site immunoenzymometric assay (Tosoh Bioscience, South San Francisco, Calif.) at the $HbA_{1c}$ was measured using ion-exchange high performance liquid chromatography (Variant II, Bio-Rad Diagnostics, Hercules, Calif.). Reliability coefficients for each assay were above 0.99 from split duplicate samples. EBV and CMV viral loads were measured in whole blood at the University of Colorado using previously described methods[1].

Flow Cytometry

Peripheral blood mononuclear cells (PBMC) were processed and stored at the NIDDK repository. Frozen vials of PBMC were sent to Benaroya Research Institute for analysis by flow cytometry with antibody panels shown in FIG. 4. T-cell phenotyping was performed on PBMC as previously described on an LSR-Fortessa (BD Biosciences) with FACS Diva software and analyzed with FlowJo software version 9.5 (Tree Star, Ashland, Oreg.). The frequency of CD8+ T-cells that were TIGIT+KLRG+CD57−, TIGIT−KLRG1−CD57−, or CD4+CD127$^{lo}$ Foxp3+(CD4+Tregs) were determined as described previously[2]. The quadrants were placed based on staining controls.

Trial Oversight

The study was developed and conducted by Type 1 Diabetes TrialNet, funded by the National Institutes of Health and the Juvenile Diabetes Research Foundation.

The study coordination, laboratory tests, and data management were conducted centrally, with the exception of CBC and differentials and routine chemistries that were analysed at the infusion sites. An independent medical monitor (masked to treatment assignment) reviewed all accruing safety data.

Statistical Analysis

The cumulative incidence of diabetes onset over time since randomization within each group was estimated from a Kaplan-Meier estimate of the "diabetes-free" survival function[16]. The difference between treatment groups in the 6-month interval cumulative incidence functions was estimated by the hazard ratio (HR) and hypothesis tests employed the likelihood ratio test; both based on the Cox Proportional Hazards (PH) model[17]. The critical value for the test statistic for the primary hypothesis was determined by a group-sequential procedure.

Because of slower than expected accrual rates, the original protocol (n=144 subjects was revised to detect a 60% (previously 50%) decrease in the hazard rate (HR=0.4) with 80% statistical power at an alpha level of 0.025 (one-sided). This set the study goal to enroll at least 71 subjects and follow them until 40 subjects were diagnosed with TID[18].

Data on safety and efficacy were evaluated twice yearly by an independent Data Safety Monitoring Board (DSMB). An interim analysis was conducted when 50% of the expected number of T1D cases was observed at which time a formal comparison was presented to the DSMB and Lan DeMets stopping rules were employed[19]. Data were analyzed according to the intention-to-treat principle. Tests of significance reported herein were one-sided using a threshold of significance of 0.025 in accordance with the design but were two-sided for treatment interaction tests. Unless indicated, 95% confidence intervals are reported. Flow cytometry data were analyzed by a repeated measures ANOVA. Statistical analyses were performed using either TIBCO Spotfire S+8.2 Workbench or SAS 9.4.

Results

Patients: Of the 112 subjects screened for eligibility, 76 were enrolled: 44 were randomized to teplizumab and 32 to placebo (FIG. 1). The randomization process resulted in unequal proportions in the study groups, probably explained by study sites with a small number of enrolled subjects (<3) in whom randomization may have resulted in unequal distribution between the arms. All participants had at least 2+ autoantibodies and 71% of the participants had 3 or more. The treatment arms were generally well balanced (Table 1). The majority of subjects (55, 72%) were children and about half were siblings of patients with T1D. Of the subjects <age 18, 47 confirmed a dysglycemic OGTT prior to randomization. Of those randomized after a single dysglycemic OGTT, 2 had "diabetic" and 6 had normal pre-treatment OGTTs: these 8 individuals were enrolled on the basis of the dysglycemia OGTT prior to enrollment.

Ninety-three percent (41/44) and 87.5% (28/32) of subjects randomized to the teplizumab and placebo groups, respectively, completed the 14 days of drug therapy. The total dose of teplizumab administered was $9.^{14}$ (IQR:9.01-9.37) µg/m$^2$. Three drug-treated and 4 placebo-treated subjects did not complete treatment because of laboratory abnormalities (n=4), inability to establish intravenous access (n=2), or rash (n=1). Median follow-up was 745 days (range 74-2683 days). The duration of follow up was more than 3 years in 75% of subjects. T1D was diagnosed in 42 (55%) of the participants.

Figure 2A:
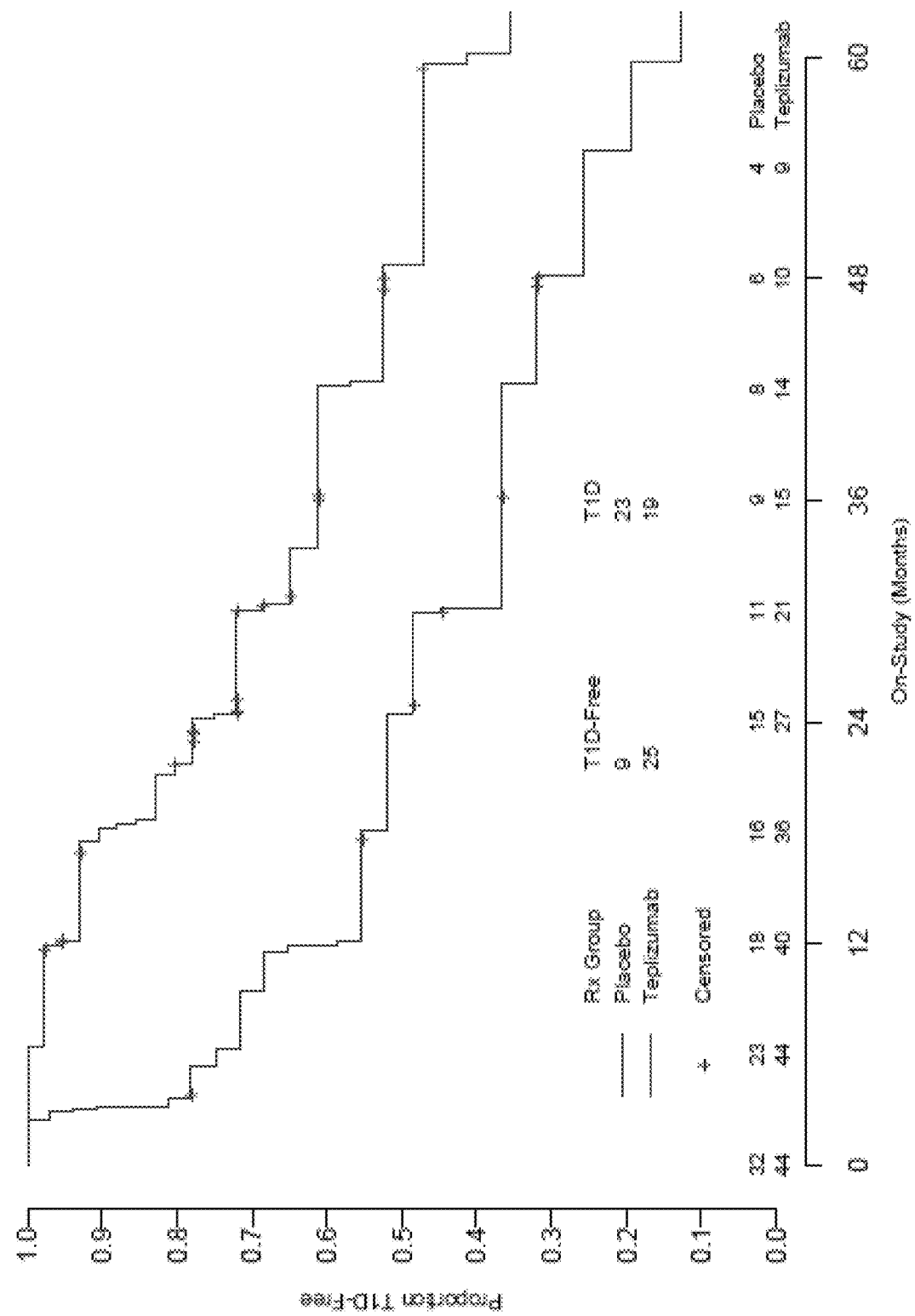
Figure 2C:
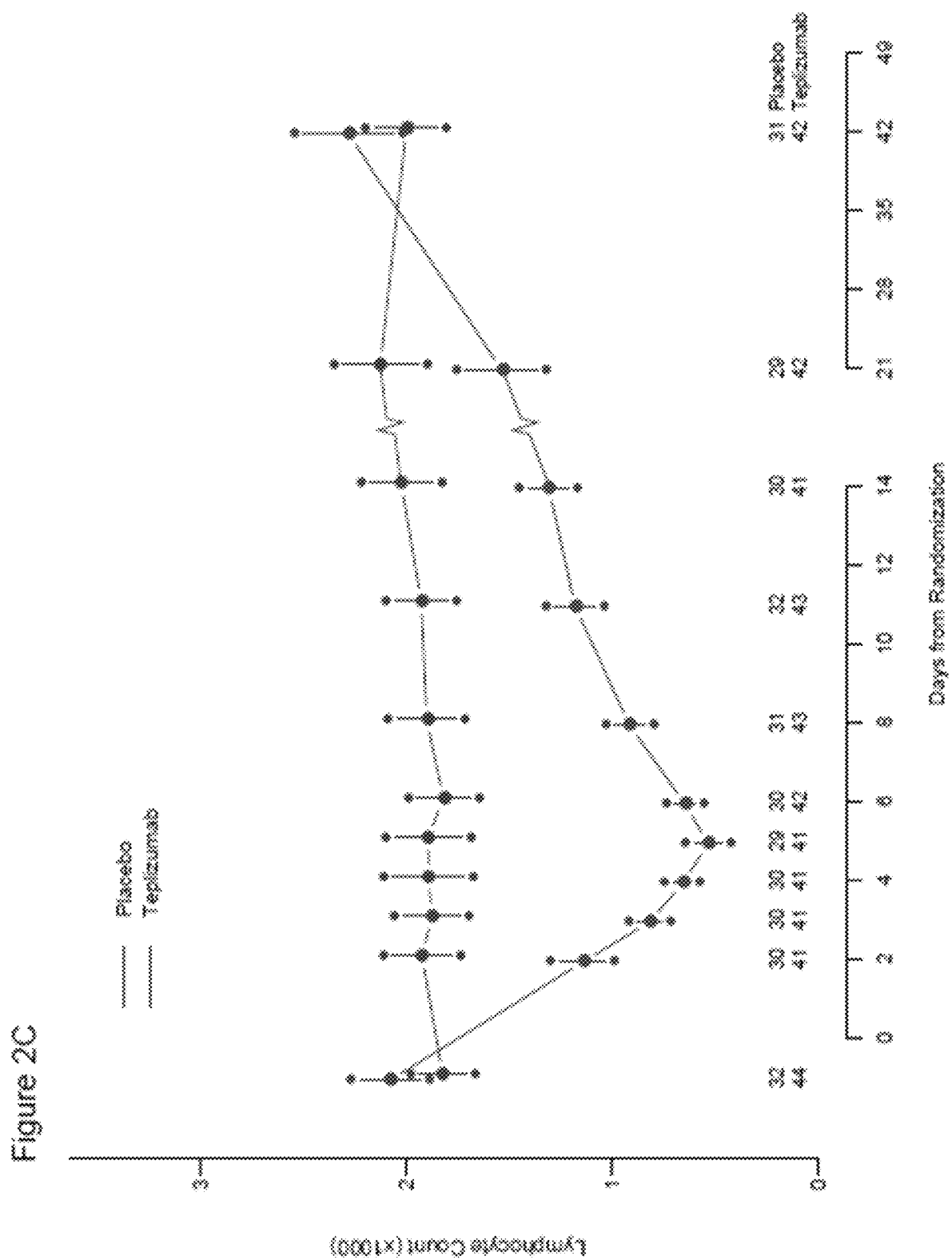

Efficacy: Treatment with a single course of teplizumab delayed the time to T1D (FIG. 2A, p=0.006): The median times to T1D was 24.4 mos in the placebo and 48.4 mos in the teplizumab groups (hazard ratio=0.437 (IQR: 0.229, 0.832). The annualized rate of T1D development was 9.8% and 4.1% for the placebo and teplizumab groups, respectively. Twenty-five (57%) subjects from the teplizumab and 9 (28%) of the placebo group were T1D-free at the conclusion of the trial (Chi-squared, p=0.012). The hazard ratio remained statistically different when adjusted for prespecified covariates of age, glucose during the OGTT prior to randomization, or anti-GAD65 antibody.

The overall rate of progression to T1D was greatest in the first year after entry into the trial (n=17, 41%) compared to year 2 (n=10, 24%), 3, (n=6, 14%), or 4 (n=5, 12%). The effect of the teplizumab treatment was also greatest during that time (FIG. 1B). The hazard ratios were lowest in the first 36 months after study enrollment and remained relatively constant and statistically significant (p<0.01) after that time.

Treatment administration and safety: In general, teplizumab treatment was well tolerated—adverse events designated as possibly, probably, or definitely related to study drug are shown in Table 2. The lymphocyte count declined to a nadir on day 5 by 72.3% (IQR 82.1, 68.4%)(p<0.0001) but recovered quickly afterwards. Fifteen (34.1%) of the grade 3 events in the teplizumab group involved lymphopenia during the first 30 days after study drug administration. There were no cases of lymphopenia after day 30 in either treatment arms (FIG. 1C). A spontaneously resolving rash, as previously noted, occurred in 36% of drug treated subjects[11]. The rates of infection were similar in the two treatment arms.

At entry, 30 subjects (39%) (16 teplizumab and 14 placebo treated) had antibodies against EBV virus. After study drug treatment, week 3-6, there were quantifiable EBV viral loads in 7 participants—all were in the teplizumab group. Of those with detectable viral loads, 1 had symptoms of pharyngitis, rhinorrhea, and cough on day 38. The EBV viral loads decreased to below the level of quantification between day 43 and 134 (average 74 days). At entry, 17 participants (10 teplizumab and 7 placebo) had antibodies against the CMV virus. One teplizumab subject, who was CMV seropositive, had detectable levels of CMV virus at day 20 that was undetectable by day 42.

Figure 3A:
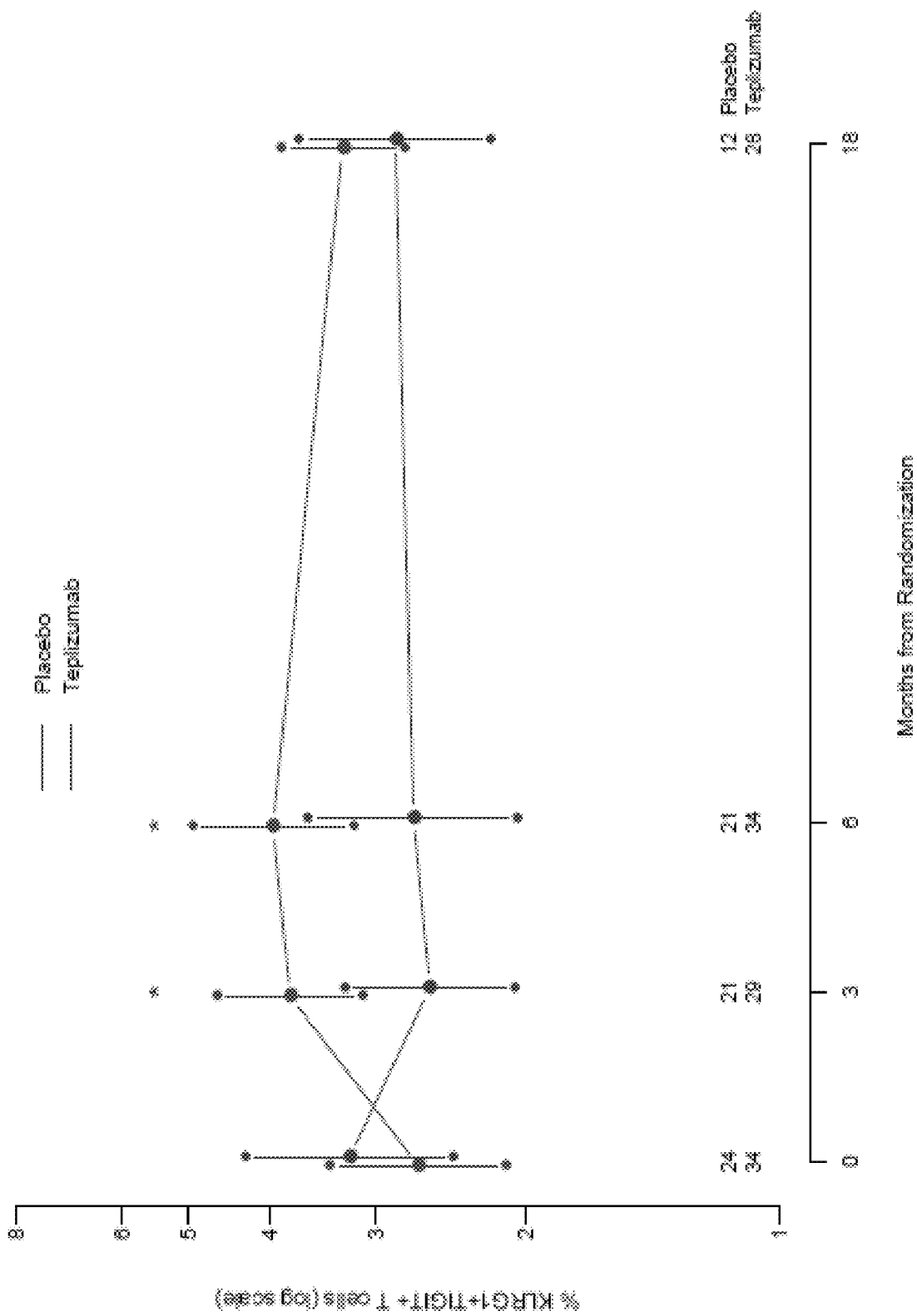
Figure 7A:
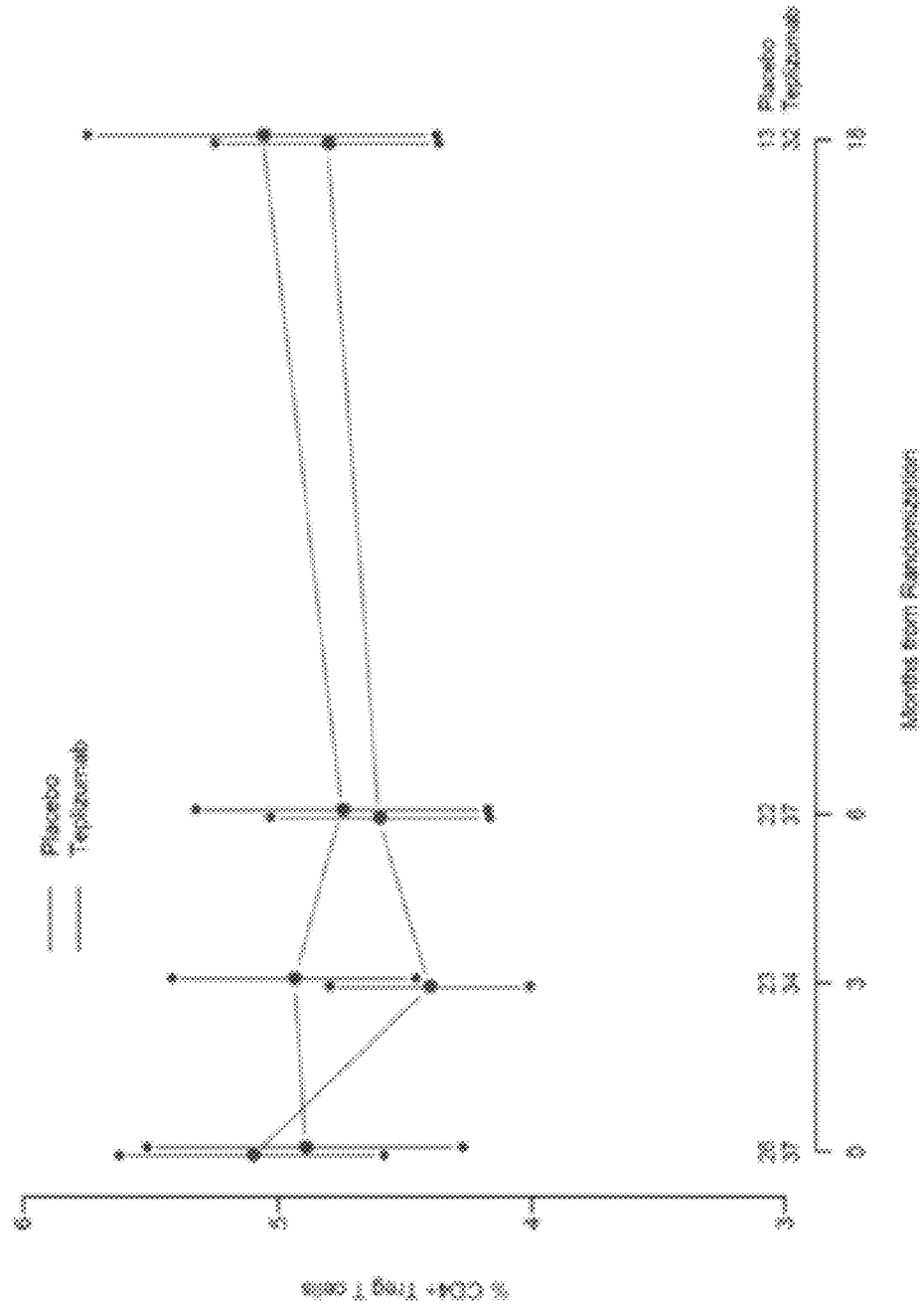
FIGS. 7A-7B: Frequency of T cell subsets in the treatment groups. The frequency of CD4+ Tregs (FIG. 7A) CD4+ CD127$_{lo}$Foxp3+ and (FIG. 7B) CD8+TIGIT-KLRG1-CD57− T cells at the study visits is shown. The differences in both cell subsets between teplizumab and placebo and from baseline to after treatment for each treatment arm were not statistically significant when compared by ANCOVA for each time point and corrected for the baseline values.
Figure 7B:
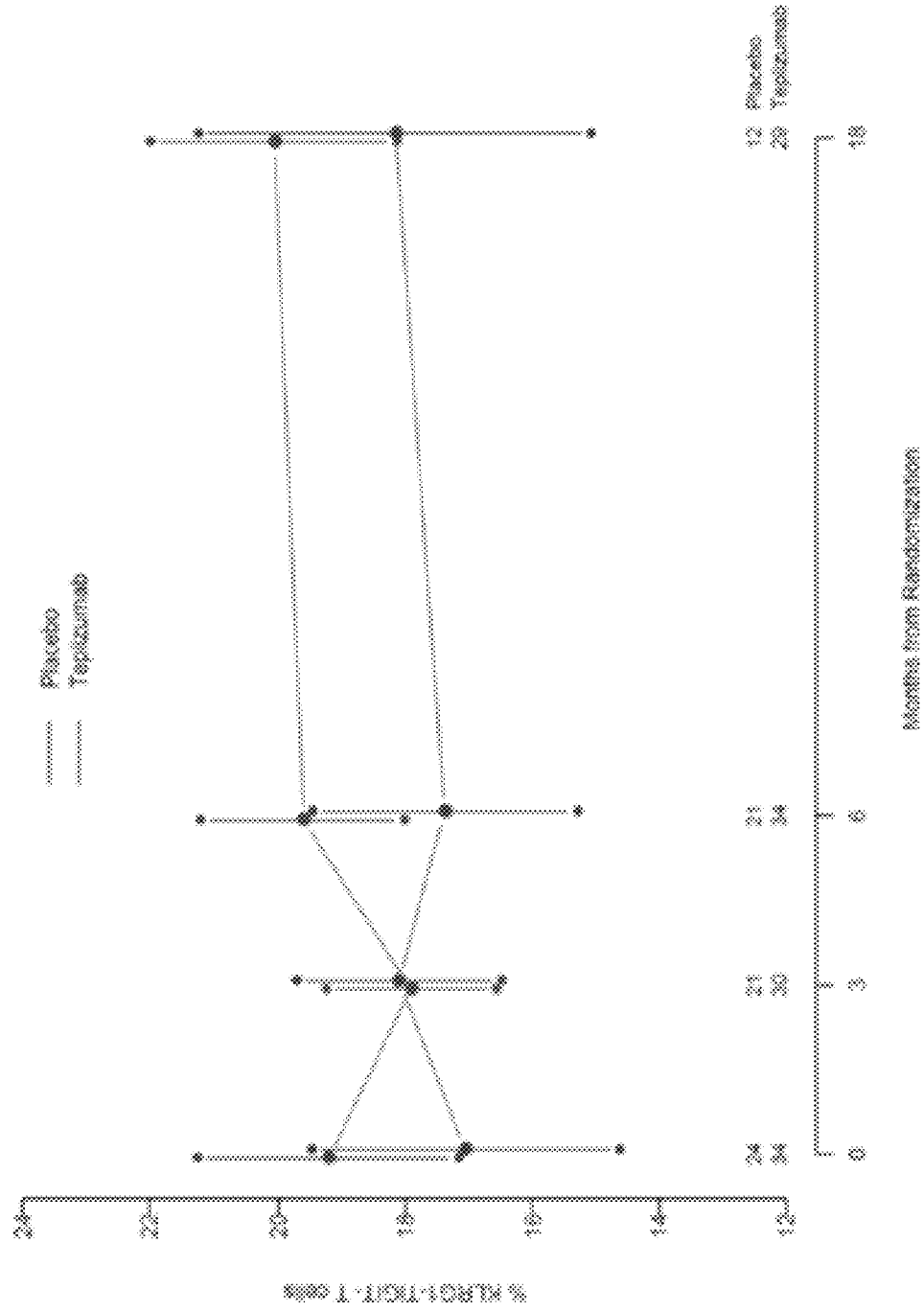

Response biomarkers: We previously described changes in CD8+ T-cells such as expression of markers associated with reduced responsiveness TIGIT, KLRG1, and others, after teplizumab treatment[12,13]. To determine whether the clinical outcomes were associated with these changes in CD8+ T-cells, we compared the frequency of CD8+ KLRG1+TIGIT+CD57− T-cells in the two treatment arms. Teplizumab treatment increased the frequency of these T-cells at month 3 and 6 compared to the baseline (p=0.009, 0.007 respectively) and the levels were higher in the teplizumab vs placebo treated participants at 3 mos and 6 mos (p=0.02, 0.04 respectively). (FIG. 3A, FIG. 6). We did not identify a change in these cells in the placebo treated subjects. Not all T-cell subsets were affected with teplizumab: There was not a significant change in CD4+ Tregs or CD8+KLRG1-TIGIT-CD57− cells in either group[8,20] (FIGS. 7A, 7B).

Figure 3B:
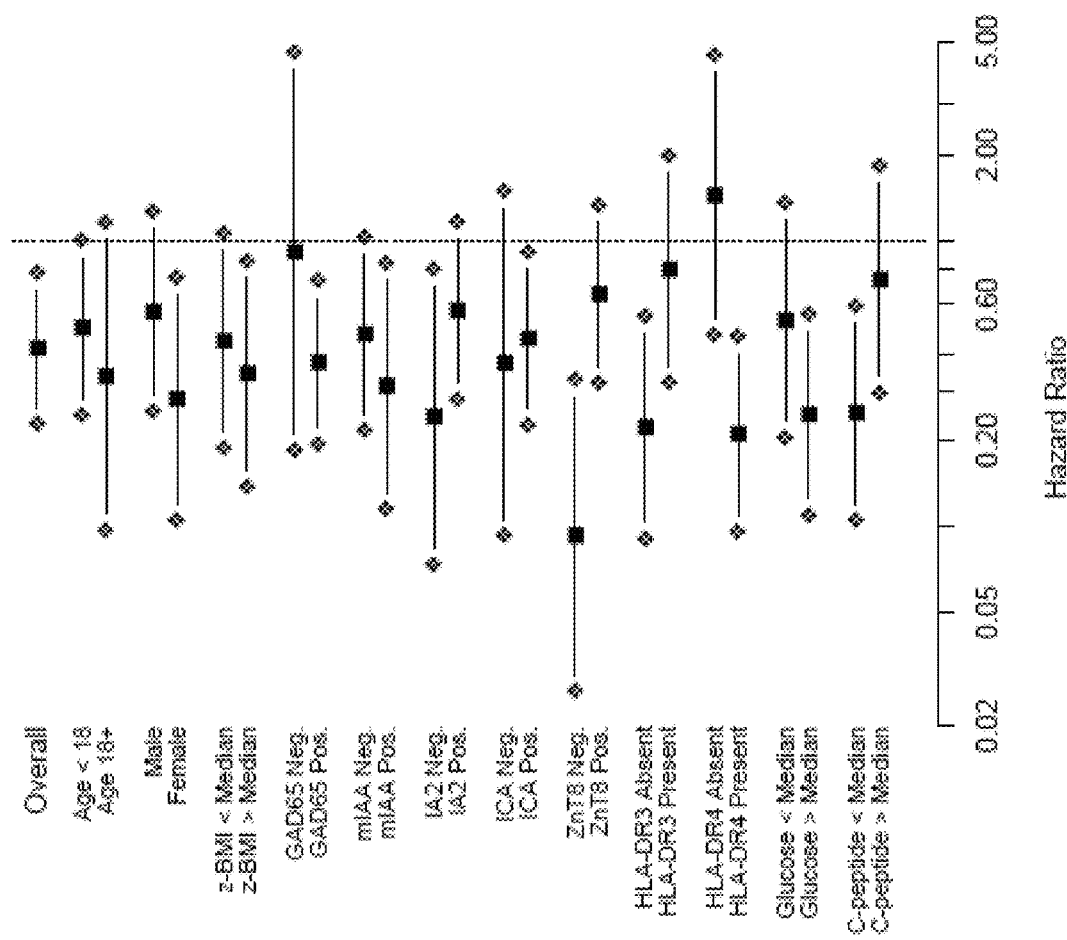

To determine whether demographic characteristics of participants were associated with clinical responses, in a prespecified analysis, we analyzed the effects of teplizumab in subgroups of participants on the basis of age, HLA type, pre-treatment C-peptide and glucose during the OGTT, and autoantibodies (FIG. 3B). Participants who did not have anti-ZnT8 antibodies showed a greater response to teplizumab compared to those who did (p=0.004)(FIG. 3C). The presence or absence of other autoantibodies was not associated with the clinical responses. 49% and 65% of the teplizumab subjects were HLA-DR3 and HLA-DR4 respectively. The presence of HLA-DR4 and absence of HLA-DR3 were associated with more robust responses to teplizumab (p=0.004 and 0.01, respectively, two-sided tests) (FIG. 3D, E).

Discussion

In this Phase II study, we found that a single course of teplizumab significantly slowed progression to T1D in non-diabetic relatives who had abnormal glucose tolerance during an OGTT at study entry. The median delay in the diagnosis of diabetes was 2 years, and at the conclusion of the trial, the frequency of diabetes-free individuals was double in the drug (57%) vs placebo-treated subjects (28%). The safety experience in children and adults was good with expected adverse events of rash and transient lymphopenia. To our knowledge, this is the first therapy that has delayed or prevented the onset of T1D. The delay in onset of clinical T1D with the challenges of daily management is of clinical importance. Moreover, a younger age of diagnosis is associated with worse outcomes[2,4]. Prior large well designed but unsuccessful prevention trials have not utilized immunotherapy directed against immune cells, and our findings support the notion that T1D is a chronic T-cell mediated disease[21,22]. Furthermore, the observation that this therapy impacts disease progression before, and loss of beta cell function after diagnosis suggests that there is a continuum in the autoimmune process, and validates the effort to use immunomodulation prior to the onset of clinical disease[9-11,23-25].

The effects of the drug were greatest in the first three years after administration. Forty-one percent of those who developed diabetes did so in the first year after randomization and the HR was lowest at that time for those exposed to teplizumab. The relatively rapid rate of progression to diabetes in the placebo group reflects the very high risk of these individuals[5]. Indeed, our decision to enroll these subjects, who did not have clinical disease, reflects the inevitability of progression when >2 autoantibodies and dysglycemia are found consistent with our report of high rates of beta cell killing in these individuals[26]. In addition, the rapid development of clinical T1D may reflect the enrichment of pediatric participants (72.4%) in whom the rate of progression is rapid[27,28].

There were differences in the responses to teplizumab based on characteristics of the subjects at the time of study enrollment. The absence of one T1D-associated MHC allele, HLA-DR3, but the presence of another, HLA-DR4, and absence of anti-ZnT8 antibodies identified individuals who were most likely to respond. The MHC may modulate responsiveness to teplizumab through its effect on the T-cell repertoire, perhaps altering T-cell activation status and susceptibility to the drug effects. It is also possible that anti-ZnT8 antibodies are a marker for individuals with a more fulminant immune response, or other features that make their T-cells susceptible to teplizumab. We cannot be certain whether the treatment will be effective in those at earlier stages of the disease. Further immunologic and metabolic studies may identify features that define individuals who are most likely to benefit from this treatment.

The transient effects of the drug treatment on lymphocyte counts most likely reflects egress from the peripheral blood rather than cell depletion[29,30]. Our flow cytometry studies suggest that changes in the phenotype of CD8+ T-cells are a marker of clinical responses. These effects, associated with a non-responsive or "exhausted" phenotype, however, do not render the CD8+ T-cells inactive since there was a brisk response to EBV and CMV in those in whom there was an increase in viral load[31,32]. The functional effects of teplizumab on T-cells may be affected by their avidity for antigen: T-cells with a high avidity, e.g. viral antigen reactive cells may be unaffected while those with low avidity e.g. autoreactive T-cells, may be rendered inactive. Further studies with antigen reactive T-cells will be needed to address this hypothesis.

There are a few limitations to this clinical study to be considered. The cohort was relatively small and the rate of progression to T1D was rapid in the placebo group. The study subjects were relatives of patients with T1D, and therefore, we do not know whether these findings will be generally applicable to non-relatives who are found to be at-risk for T1D. Recent reports suggest that in genetically high risk individuals, the rates of diabetes are similar in non-relatives and relatives[33]. Moreover, while reflecting the known incidence of disease, the population was overwhelmingly non-hispanic Caucasians. Increasing the median delay in disease onset would be ideal. In this study, the drug was only given for one course and our analysis of the HR suggests that repeated dosing may be needed to capture more individuals with active disease and to prolong the therapeutic effect[9,25]. Identifying the target population for treatment and the number of drug courses need to be explored.

In summary, this is the first trial to show delay or prevention of T1D. Because age of onset and duration of diabetes are important determinants for metabolic management and complications, and the daily burden of management, any time without diabetes has clinical significance. Selection of those who are most likely to respond, repeated dosing, or combinations of teplizumab with other agents with complementary mechanisms of action may enable prevention of clinical disease for extended periods of time.

TABLE 1

Subject characteristics at baseline by treatment group

| Subject Characteristic and Descriptive Statistic* Displayed | Teplizumab N = 44 | Placebo N = 32 |
|---|---|---|
| Age - years | | |
| Median | 14 (12-22) | 13 (11-6) |
| Range | 8.5-49.5 | 8.6-45.0 |
| Male sex | | |
| No. of subjects | 25 (56.8) | 17 (53.1) |
| Race - No. of subjects | | |
| White | 44 (100.0) | 30 (93.8) |
| African American | 0 (0.0) | 0 (0.0) |
| Asian | 0 (0.0) | 2 (6.2) |
| Ethnicity - No. of subjects | | |
| Non-Hispanic | 43 (97.7) | 31 (96.9) |
| Relationship to index case - No. of subjects | | |
| Sibling(s) | 24 (54.5) | 16 (50.0) |
| Identical twin | 4 (9.1) | 0 (0.0) |
| Offspring | 6 (13.6) | 6 (18.8) |
| Parent | 6 (13.6) | 3 (9.4) |
| Sibling and another first degree | 2 (4.5) | 3 (9.4) |
| Second degree | 2 (4.5) | 3 (9.4) |
| Third degree or further removed | 0 (0.0) | 1 (3.1) |
| Autoantibodies Positive - No. of subjects | | |
| Anti-GAD65 (harmonized) | 40 (90.9) | 28 (87.5) |
| Micro Insulin | 20 (45.5) | 11 (34.4) |
| Anti-IA-2 (harmonized) | 27 (61.4) | 24 (75.0) |
| ICA | 29 (65.9) | 28 (87.5) |
| Zinc Transporter | 32 (72.7) | 24 (75.0) |
| Autoantibodies titer - median | | |
| Anti-GAD65 (harmonized) | 240 (76.8-464) | 221 (42.3-520) |
| Micro Insulin | 0.0070 (0.0020-0.028) | 0.0040 (0.0020-0.0168) |
| Anti-IA-2 (harmonized) | 52 (0-310) | 187 (26-253) |
| ICA | 20 (0-200) | 80 (20-160) |
| Zinc Transporter | 0.157 (0.0133-0.496) | 0.096 (0.028-0.386) |

TABLE 1-continued

Subject characteristics at baseline by treatment group

| No. of Autoantibodies Positive^ | | |
|---|---|---|
| 1 | 4 (9.1) | 0 (0.0) |
| 2 | 11 (25.0) | 7 (21.9) |
| 3 | 14 (31.8) | 10 (31.3) |
| 4 | 15 (34.1) | 15 (46.9) |
| Glycated hemoglobin - percent | | |
| Median | 5.2 (4.9-5.4) | 5.3 (5.1 -5.4) |
| Body Mass Index (kg/m2) | | |
| Median | 19.6 (17.3-25.4) | 21.5 (18.2-24.7) |
| Z-score BMI | 0.259 (−0.754-1.19) | 0.681 (0.339-1.11) |
| C-peptide AUC Mean, OGTT † (nmol/L) | | |
| Median | 1.76 (1.47-2.18) | 1.73 (1.44-2.36) |
| HLA alleles present † - no. of subjects (%) | | |
| Neither DR3 or DR4 | 5 (11.6) | 3 (9.4) |
| DR3 only | 10 (23.3) | 8 (25.0) |
| DR4 only | 17 (39.5) | 14 (43.8) |
| Both | 11 (25.6) | 7 (21.9) |

| Subject Characteristic and Descriptive Statistic* Displayed | Anti-CD3 MAB N = 44 | Placebo N = 32 |
|---|---|---|
| Age - years | | |
| Median | 14 (12-22) | 13 (11-16) |
| Range | 8.5-49.5 | 8.6-45.0 |
| Male sex | | |
| No. of subjects | 25 (56.8) | 17 (53.1) |
| Race - No. of subjects | | |
| White | 44 (100.0) | 30 (93.8) |
| African American | 0 (0.0) | 0 (0.0) |
| Asian | 0 (0.0) | 2 (6.2) |
| Ethnicity - No. of subjects | | |
| Non-Hispanic | 43 (97.7) | 31 (96.9) |
| Relationship to index case - No. of subjects | | |
| Sibling(s) | 24 (54.5) | 16 (50.0) |
| Identical twin | 4 (9.1) | 0 (0.0) |
| Offspring | 6 (13.6) | 6 (18.8) |
| Parent | 6 (13.6) | 3 (9.4) |
| Sibling and another first degree | 2 (4.5) | 3 (9.4) |
| Second degree | 2 (4.5) | 3 (9.4) |
| Third degree or further removed | 0 (0.0) | 1 (3.1) |
| Autoantibodies Positive - No. of subjects | | |
| Anti-GAD65 (harmonized) | 40 (90.9) | 28 (87.5) |
| Micro Insulin | 20 (45.5) | 11 (34.4) |
| Anti-IA-2 (harmonized) | 27 (61.4) | 24 (75.0) |
| ICA | 29 (65.9) | 28 (87.5) |
| Zinc Transporter | 32 (72.7) | 24 (75.0) |
| Autoantibodies titer - median | | |
| Anti-GAD65 (harmonized) | 240 (76.8-464) | 221 (42.3-520) |
| Micro Insulin | 0.0070 (0.0020-0.028) | 0.0040 (0.0020-0.0168) |
| Anti-IA-2 (harmonized) | 52 (0-310) | 187 (26-253) |
| ICA | 20 (0-200) | 80 (20-160) |
| Zinc Transporter | 0.157 (0.0133-0.496) | 0.096 (0.028-0.386) |
| No. of Autoantibodies Positive^ | | |
| 1 | 4 (9.1) | 0 (0.0) |
| 2 | 11 (25.0) | 7 (21.9) |
| 3 | 14 (31.8) | 10 (31.3) |
| 4 | 15 (34.1) | 15 (46.9) |
| Glycated hemoglobin - percent | | |
| Median | 5.2 (4.9-5.4) | 5.3 (5.1-5.4) |

TABLE 1-continued

Subject characteristics at baseline by treatment group

| Body Mass Index (kg/m²) | | |
|---|---|---|
| Median | 19.6 (17.3-25.4) | 21.5 (18.2-24.7) |
| Z-score BMI | 0.259 (−0.754-1.19) | 0.681 (0.339-1.11) |
| C-peptide AUC Mean, OGTT † (nmol/L) | | |
| Median | 1.76 (1.47-2.18) | 1.73 (1.44-2.36) |
| HLA alleles present † - no. of subjects (%) | | |
| Neither DR3 or DR4 | 5 (11.6) | 3 (9.4) |
| DR3 only | 10 (23.3) | 8 (25.0) |
| DR4 only | 17 (39.5) | 14 (43.8) |
| Both | 11 (25.6) | 7 (21.9) |

*Parenthetical value(s): The interquartile range is displayed with the median, and percent of subjects is displayed with the number of subjects.
^at the time of randomization. All subjects had at least 2+ autoantibodies prior to randomization.
† Missing: HLA allele status missing for 1 subject

TABLE 2

Adverse events designated as possibly, probably, or definitely related to study drug during active follow-up

| | Teplizumab | | Placebo | |
|---|---|---|---|---|
| Adverse Effect Category | No. of Events | No. of Subjects | No. of Events | No. of Subjects |
| Blood/Bone Marrow*** | 45 | 33 (75) | 2 | 2 (6.2) |
| Dermatology/Skin*** | 17 | 16 (36.4) | 1 | 1 (3.1) |
| Pain | 11 | 5 (11.4) | 5 | 3 (9.4) |
| Infection | 8 | 5 (11.4) | 5 | 3 (9.4) |
| Gastrointestinal | 5 | 4 (9.1) | 3 | 3 (9.4) |
| Metabolic/Laboratory | 7 | 4 (9.1) | 2 | 2 (6.2) |
| Pulmonary/Upper Respiratory | 6 | 4 (9.1) | 0 | 0 (0) |
| Constitutional Symptoms | 3 | 2 (4.5) | 0 | 0 (0) |
| Allergy/Immunology | 2 | 2 (4.5) | 0 | 0 (0) |
| Cardiac General | 1 | 1 (2.3) | 1 | 1 (3.1) |
| Endocrine | 0 | 0 (0) | 2 | 2 (6.2) |
| Vascular | 1 | 1 (2.3) | 1 | 1 (3.1) |
| Neurology | 1 | 1 (2.3) | 0 | 0 (0) |
| Ocular/Visual | 1 | 1 (2.3) | 0 | 0 (0) |
| Musculoskeletal/Soft Tissue | 2 | 1 (2.3) | 0 | 0 (0) |
| Hepatobiliary/Pancreas | 0 | 0 (0) | 1 | 1 (3.1) |
| Syndromes | 1 | 1 (2.3) | 0 | 0 (0) |
| Hemorrhage/Bleeding | 1 | 1 (2.3) | 0 | 0 (0) |
| Total Events and Subjects | 112 | 44 (100) | 23 | 32 (100) |

***p < 0.001 Teplizumab vs placebo

Modifications and variations of the described methods and compositions of the present disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure are intended and understood by those skilled in the relevant field in which this disclosure resides to be within the scope of the disclosure as represented by the following claims.

INCORPORATION BY REFERENCE

All patents and publications mentioned in this specification are herein incorporated by reference to the same extent as if each independent patent and publication was specifically and individually indicated to be incorporated by reference.

REFERENCES

1. Menke A, Orchard T J, Imperatore G, Bullard K M, Mayer-Davis E, Cowie C C. The prevalence of type 1 diabetes in the United States. Epidemiology 2013; 24:773-4.
2. Miller K M, Foster N C, Beck R W, et al. Current state of type 1 diabetes treatment in the U.S.: updated data from the T1D Exchange clinic registry. Diabetes Care 2015; 38:971-8.
3. Livingstone S J, Levin D, Looker H C, et al. Estimated life expectancy in a Scottish cohort with type 1 diabetes, 2008-2010. JAMA 2015; 313:37-44.
4. Rawshani A, Sattar N, Franzen S, et al. Excess mortality and cardiovascular disease in young adults with type 1 diabetes in relation to age at onset: a nationwide, register-based cohort study. Lancet 2018; 392:477-86.
5. Insel R A, Dunne J L, Atkinson M A, et al. Staging presymptomatic type 1 diabetes: a scientific statement of JDRF, the Endocrine Society, and the American Diabetes Association. Diabetes Care 2015; 38:1964-74.
6. Atkinson M A, Roep B O, Posgai A, Wheeler D C S, Peakman M. The challenge of modulating beta-cell autoimmunity in type 1 diabetes. Lancet Diabetes Endocrinol 2019; 7:52-64.
7. Keymeulen B, Vandemeulebroucke E, Ziegler A G, et al. Insulin needs after CD3-antibody therapy in new-onset type 1 diabetes. N Engl J Med 2005; 352:2598-608.
8. Perdigoto A L, Preston-Hurlburt P, Clark P, et al. Treatment of Type 1 diabetes with teplizumab: clinical and immunological follow-up after 7 years from diagnosis. Diabetologia in press.
9. Herold K C, Gitelman S E, Ehlers M R, et al. Teplizumab (anti-CD3 mAb) treatment preserves C-peptide responses in patients with new-onset type 1 diabetes in a randomized controlled trial: Metabolic and immunologic features at baseline identify a subgroup of responders. Diabetes 2013.
10. Hagopian W, Ferry R J, Jr., Sherry N, et al. Teplizumab preserves C-peptide in recent-onset type 1 diabetes: two-year results from the randomized, placebo-controlled Protege trial. Diabetes 2013; 62:3901-8.
11. Herold K C, Hagopian W, Auger J A, et al. Anti-CD3 monoclonal antibody in new-onset type 1 diabetes mellitus. N Engl J Med 2002; 346:1692-8.

12. Tooley J E, Vudattu N, Choi J, et al. Changes in T-cell subsets identify responders to FcR non-binding anti-CD3 mAb (teplizumab) in patients with Type 1 diabetes. Eur J Immunol 2015.
13. Long S A, Thorpe J, DeBerg H A, et al. Partial exhaustion of CD8 T cells and clinical response to teplizumab in new-onset type 1 diabetes. Sci Immunol 2016; 1.
14. Bingley P J, Wherrett D K, Shultz A, Rafkin L E, Atkinson M A, Greenbaum C J. Type 1 Diabetes TrialNet: A Multifaceted Approach to Bringing Disease-Modifying Therapy to Clinical Use in Type 1 Diabetes. Diabetes Care 2018; 41:653-61.
15. American Diabetes A. 2. Classification and Diagnosis of Diabetes: Standards of Medical Care in Diabetes-2019. Diabetes Care 2019; 42:S13-S28.
16. Therneau T, Grambsch P. Modeling survival data: extending the Cox Model. New York: Springer-Verlag; 2000.
17. Cox D. Regression model and life tables. J R Stat Soc Ser C Appl Stat 1972; 34B:187-220.
18. Schoenfeld D A. Sample-size formula for the proportional-hazards regression model. Biometrics 1983; 39:499-503.
19. K. K. L, DeMets D. Discrete sequential boundaries for clinical trials. Biometrika 1983; 70:659-63.
20. Herold K C, Burton J B, Francois F, Poumian-Ruiz E, Glandt M, Bluestone J A. Activation of human T cells by FcR nonbinding anti-CD3 mAb, hOKT3gamma1(Ala-Ala). J Clin Invest 2003; 111:409-18.
21. Effects of insulin in relatives of patients with type 1 diabetes mellitus. N Engl J Med 2002; 346:1685-91.
22. Gale E A, Bingley P J, Emmett C L, Collier T. European Nicotinamide Diabetes Intervention Trial (ENDIT): a randomised controlled trial of intervention before the onset of type 1 diabetes. Lancet 2004; 363:925-31.
23. Herold K C, Gitelman S E, Masharani U, et al. A Single Course of Anti-CD3 Monoclonal Antibody hOKT3 {gamma} 1(Ala-Ala) Results in Improvement in C-Peptide Responses and Clinical Parameters for at Least 2 Years after Onset of Type 1 Diabetes. Diabetes 2005; 54:1763-9.
24. Perdigoto A L, Preston-Hurlburt P, Clark P, et al. Treatment of type 1 diabetes with teplizumab: clinical and immunological follow-up after 7 years from diagnosis. Diabetologia 2018.
25. Sherry N, Hagopian W, Ludvigsson J, et al. Teplizumab for treatment of type 1 diabetes (Protege study): 1-year results from a randomised, placebo-controlled trial. Lancet 2011.
26. Herold K C, Usmani-Brown S, Ghazi T, et al. beta Cell death and dysfunction during type 1 diabetes development in at-risk individuals. J Clin Invest 2015; 125:1163-73.
27. Greenbaum C J, Beam C A, Boulware D, et al. Fall in C-peptide During First 2 Years From Diagnosis: Evidence of at Least Two Distinct Phases From Composite TrialNet Data. Diabetes 2012.
28. Wherrett D K, Chiang J L, Delamater A M, et al. Defining pathways for development of disease-modifying therapies in children with type 1 diabetes: a consensus report. Diabetes Care 2015; 38:1975-85.
29. Esplugues E, Huber S, Gagliani N, et al. Control of TH17 cells occurs in the small intestine. Nature 2011; 475:514-8.
30. Waldron-Lynch F, Henegariu O, Deng S, et al. Teplizumab induces human gut-tropic regulatory cells in humanized mice and patients. Sci Transl Med 2012; 4:118ra12.
31. Wherry E J. T cell exhaustion. Nature Immunology 2011; 12:492.
32. Wherry E J, Ha S J, Kaech S M, et al. Molecular signature of CD8+ T cell exhaustion during chronic viral infection. Immunity 2007; 27:670-84.
33. Hippich M, Beyerlein A, Hagopian W A, et al. Genetic Contribution to the Divergence in Type 1 Diabetes Risk Between Children From the General Population and Children From Affected Families. Diabetes 2019.
34. Mantel N. Evaluation of survival data and two new rank order statistics arising in its consideration. Cancer Chemother Rep 1966; 50:163-70.

The invention claimed is:

1. A method of preventing or delaying the onset of clinical type I diabetes (T1D), comprising:
   providing a non-diabetic subject who is (1) in an immunospecific assay, free of antibodies against zinc transporter 8 (ZnT8), (2) HLA-DR4+, and (3) not HLA-DR3+; and
   administering an agent comprising a prophylactically effective amount of teplizumab to the non-diabetic subject.

2. The method of claim 1, further comprising determining that the non-diabetic subject is (1), in an immunospecific assay, free of antibodies against zinc transporter 8(ZnT8), (2) HLA-DR4+, and (3) not HLA-DR3+.

3. The method of claim 1, wherein the non-diabetic subject is a relative of a patient with T1D.

4. The method of claim 1, wherein the non-diabetic subject has two or more diabetes-related autoantibodies selected from islet cell antibodies (ICA), insulin autoantibodies (IAA), antibodies to glutamic acid decarboxylase (GAD), or antibodies to tyrosine phosphatase (IA-2/ICA512).

5. The method of claim 1, wherein the non-diabetic subject has abnormal glucose tolerance on oral glucose tolerance test (OGTT).

6. The method of claim 5, wherein the abnormal glucose tolerance on OGTT is a fasting glucose level of 110-125 mg/dL.

7. The method of claim 5, wherein the abnormal glucose tolerance on OGTT is a 2 hour plasma of ≥140 and <200 mg/dL.

8. The method of claim 5, wherein the abnormal glucose tolerance on OGTT is a glucose value at 30, 60, or 90 minutes on OGTT>200 mg/dL.

9. The method of claim 1, wherein the prophylactically effective amount comprises a 10 to 14 day course of subcutaneous (SC) injection or intravenous (IV) infusion or oral administration of teplizumab at from about 10 to about 1000 micrograms/meter squared ($\mu g/m^2$).

10. The method of claim 1, wherein the prophylactically effective amount comprises a 10 to 14 day course of subcutaneous (SC) injection of teplizumab at about 10-1000 micrograms/meter squared ($\mu g/m^2$).

11. The method of claim 1, wherein the prophylactically effective amount comprises a 10 to 14 day course of intravenous (IV) infusion of teplizumab at about 10-1000 micrograms/meter squared ($\mu g/m^2$).

12. The method of claim 1, wherein the prophylactically effective amount comprises a 10 to 14 day course of oral administration of teplizumab at about 10-1000 micrograms/meter squared ($\mu g/m^2$).

13. The method of claim 1, wherein the prophylactically effective amount comprises a 10 to 14 day course of subcutaneous (SC) injection or intravenous (IV) infusion or oral administration of teplizumab at from about 5 to about 1200 $\mu g/m^2$.

14. The method of claim 1, wherein the prophylactically effective amount comprises a 10 to 14 day course of subcutaneous (SC) injection of teplizumab at from about 5 to about 1200 $\mu g/m^2$.

15. The method of claim 1, wherein the prophylactically effective amount comprises a 10 to 14 day course of intravenous (IV) infusion of teplizumab at from about 5 to about 1200 μg/m².

16. The method of claim 1, wherein the prophylactically effective amount comprises a 10 to 14 day course of oral administration of teplizumab at from about 5 to about 1200 μg/m².

17. The method of claim 1, wherein the prophylactically effective amount comprises a 10 to 14 day course IV infusion at about 51 μg/m² on day 0, about 103 μg/m² on day 1, about 207 μg/m² on day 2, and about 413 μg/m² on day 3, and one dose of about 826 μg/m² on each of days 4 to 13.

18. The method of claim 1, wherein the prophylactically effective amount delays median time to clinical diagnosis of T1D by from at least 50% to at least 90%.

19. The method of claim 1, wherein the prophylactically effective amount delays median time to clinical diagnosis of T1D by from at least 12 months to at least 60 months.

20. The method of claim 1, further comprising determining, by flow cytometry, a frequency of TIGIT+KLRG1+ CD8+ T-cells in peripheral blood mononuclear cells of the non-diabetic subject, wherein an increase in the frequency after administrating teplizumab indicates responsiveness to teplizumab.

* * * * *

SEQUENCE LISTING

```
<160> NUMBER OF SEQ ID NOS: 2

<210> SEQ ID NO 1
<211> LENGTH: 213
<212> TYPE: PRT
<213> ORGANISM: Unknown
<220> FEATURE:
<223> OTHER INFORMATION: Synthetic

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

Asn Trp Tyr Gln Gln Thr Pro Gly Lys Ala Pro Lys Arg Trp Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95
```

```
Phe Gly Gln Gly Thr Lys Leu Gln Ile Thr Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 2
<211> LENGTH: 449
<212> TYPE: PRT
<213> ORGANISM: Unknown
<220> FEATURE:
<223> OTHER INFORMATION: Synthetic

<400> SEQUENCE: 2

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240
```

```
Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
        290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Asp Glu Leu Thr Lys Asn Gln Val Ser Leu Thr
        355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
        435             440             445

Lys
```